US012653898B2

(12) United States Patent
Onoda et al.

(10) Patent No.: US 12,653,898 B2
(45) Date of Patent: Jun. 16, 2026

(54) POLYOXYETHYLENE DERIVATIVES AND CONJUGATES THEREOF

(71) Applicants: NATIONAL UNIVERSITY CORPORATION HOKKAIDO UNIVERSITY, Sapporo (JP); OSAKA UNIVERSITY, Suita (JP); NOF CORPORATION, Tokyo (JP)

(72) Inventors: Akira Onoda, Sapporo (JP); Takashi Hayashi, Suita (JP); Ken Hamura, Kawasaki (JP); Akira Suzuki, Kawasaki (JP); Satoshi Kishida, Kawasaki (JP)

(73) Assignees: NATIONAL UNIVERSITY CORPORATION HOKKAIDO UNIVERSITY, Sapporo (JP); OSAKA UNIVERSITY, Suita (JP); NOF CORPORATION, Tokyo (JP)

( * ) Notice: Subject to any disclaimer, the term of this patent is extended or adjusted under 35 U.S.C. 154(b) by 247 days.

(21) Appl. No.: 18/435,636

(22) Filed: Feb. 7, 2024

(65) Prior Publication Data

US 2024/0277855 A1 Aug. 22, 2024

(30) Foreign Application Priority Data

Feb. 9, 2023 (JP) ................................ 2023-018695

(51) Int. Cl.

| | |
|---|---|
| ***A61K 47/60*** | (2017.01) |
| ***A61K 47/54*** | (2017.01) |
| ***C12N 9/22*** | (2006.01) |

(52) U.S. Cl.

CPC ........... *A61K 47/60* (2017.08); *A61K 47/545* (2017.08); *C12N 9/22* (2013.01)

(58) Field of Classification Search

CPC ......... C12N 9/22; A61K 47/60; A61K 47/545

See application file for complete search history.

(56) References Cited

U.S. PATENT DOCUMENTS

| | | | |
|---|---|---|---|
| 2011/0112021 | A1 | 5/2011 | Rau et al. |
| 2022/0204481 | A1 | 6/2022 | Hayashi et al. |

FOREIGN PATENT DOCUMENTS

| | | | |
|---|---|---|---|
| JP | 2018-150311 A | 9/2018 | |
| WO | WO 2006/138572 A2 | 12/2006 | |
| WO | WO 2020/175680 A1 | 9/2020 | |

*Primary Examiner* — Tekchand Saidha

(74) *Attorney, Agent, or Firm* — Leydig, Voit & Mayer, Ltd.

(57) ABSTRACT

Polyoxyethylene derivatives represented by the following formula (1) provided by the present invention:

(1)

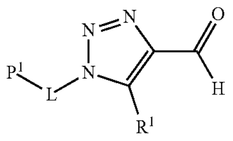

wherein the symbols in the formula are as defined in the specification, can form conjugates with polypeptide that can be degraded over a long time under physiological conditions to release the polypeptide.

10 Claims, 1 Drawing Sheet

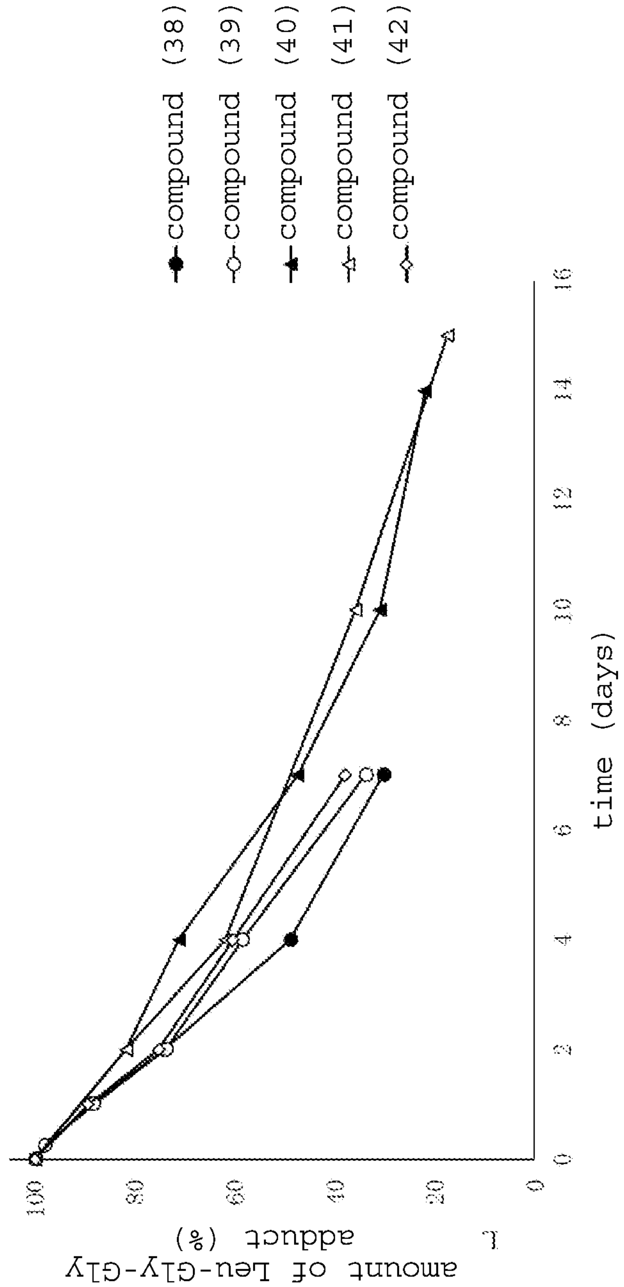
compound (38)
compound (39)
compound (40)
compound (41)
compound (42)
amount of Leu-Gly-Gly adduct (%)
100
80
60
40
20
0
0
2
4
6
8
10
12
14
16
time (days)

POLYOXYETHYLENE DERIVATIVES AND CONJUGATES THEREOF

TECHNICAL FIELD OF THE INVENTION

The present invention relates to polyoxyethylene derivatives, and conjugates of the aforementioned polyoxyethylene derivatives and polypeptides.

BACKGROUND OF THE INVENTION

When pharmaceutical products that use biofunctional molecules such as hormones, cytokines, and enzymes are administered into the body, they are generally rapidly excreted from the body through glomerular filtration in the kidneys and uptake by macrophages in the liver, spleen, and the like. Therefore, their half-life in blood is short, and it is often difficult to obtain sufficient pharmacological effects. In order to solve this problem, attempts have been made to chemically modify biofunctional molecules with water-soluble polymers such as polyethylene glycol (PEG) and the like. As a result, it becomes possible to extend the half-life in blood of biofunctional molecules and the like by increasing the molecular weight and forming a hydration layer. It is also well known that these modifications can produce effects such as reduction of the toxicity and antigenicity of biofunctional molecules and improvement of aggregation.

In biofunctional molecules chemically modified with water-soluble polymers such as PEG, moreover, interaction with target endogenous molecules and receptors may decrease due to the formation of a hydration layer and three-dimensional shielding effect of the active site by the water-soluble polymer. It is known that this may lead to unfavorable effects such as a decrease in the pharmacological action of biofunctional molecules and changes in intracorporeal and intracellular dynamics.

As an approach to the above-mentioned problems, a method of chemically modifying biofunctional molecules with water-soluble polymers via temporary bonds, and then cleaving the temporary bonds in vivo to release biofunctional molecules that are not chemically modified, namely, a prodrug formation method, is used.

In recent years, with respect to biofunctional molecules modified with water-soluble polymers, the techniques described in, for example, JP-A-2018-150311 and WO 2006/138572 are known as techniques capable of suppressing, by using prodrug formation methods, a decrease in the pharmacological action of biofunctional molecules and changes in intracorporeal and intracellular dynamics. These JP-A-2018-150311 and WO 2006/138572 report that PEGylated human growth hormone (hGH) and PEGylated insulin modified with PEG via a linker, which linker degrades at a moderate rate under physiological conditions, i.e., neutral conditions, in a non-enzyme-dependent manner to release hGH and insulin which are biofunctional molecules, release the biofunctional molecules along with the degradation of the linker, while extending the half-life in blood of the biofunctional molecules, thereby improving the pharmacological action that decreased due to the PEGylation. Therefrom a prodrug formation technique that releases biofunctional molecules at a moderate rate under physiological conditions in a non-enzyme-dependent manner while extending the half-life in blood of the biofunctional molecules to cause expression of the pharmacological action is important.

Furthermore, in order not to interfere with the effect of extending the half-life in blood of the biofunctional molecule by PEGylation, an appropriate degradation rate is required for the temporary bond. For example, the degradation half-life of human growth hormone bound to PEG via a temporary bond under physiological conditions is about 50 hr, as disclosed in JP-A-2018-150311, and the degradation half-life of insulin bound to PEG via a temporary bond under physiological conditions is about 4.5 days as disclosed in WO 2006/138572. In the present specification, the "degradation half-life" refers to the time when the temporary bond in the chemically modified biofunctional molecule is cleaved and half of the chemically modified biofunctional molecule (i.e., 0.5 mol per 1 mol of chemically modified biofunctional molecule) is released as a biofunctional molecule that has not been chemically modified.

WO 2020/175680 reports a compound in which a biofunctional molecule chemically modified with PEG cleaves the temporary bond in a non-enzyme dependent manner to release a biofunctional molecule that is not chemically modified. Specifically, WO 2020/175680 reports that an aminal bond formed by bonding a biofunctional molecule with a compound in which a formyl group is bonded to a triazole ring is gradually cleaved under physiological conditions, and the imino group generated by the cleavage is hydrolyzed to release biofunctional molecules that are not chemically modified.

SUMMARY OF THE INVENTION

Problems to be Solved by the Invention

Example 18 of WO 2020/175680 investigates the stability of the conjugate of bovine pancreas-derived ribonuclease A (RNase A) and compound 7 (1-benzyl-1H-1,2,3-triazole-4-carbaldehyde) produced in Example 10. The results shown in FIG. 54 of WO 2020/175680 show that the degradation half-life of the aforementioned conjugate under physiological conditions is as short as 12 to 18 hr. Furthermore, WO 2020/175680 does not describe a prodrug formation technique for a biofunctional molecule that can extend the degradation half-life.

The present invention aims to provide a polyoxyethylene derivative capable of forming a conjugate with a polypeptide capable of functioning as a biofunctional molecule, wherein the conjugate can be degraded over a long time under physiological conditions to release the aforementioned polypeptide (sometimes to be indicated as a "releasable polyoxyethylene derivative" in the present specification).

Means of Solving the Problems

The present inventors have conducted intensive studies and found that a conjugate with a polypeptide capable of functioning as a biofunctional molecule, wherein the conjugate can be degraded over a long time under physiological conditions to release the aforementioned polypeptide, can be formed using the below-mentioned specific releasable polyoxyethylene derivative. The present invention based on this finding is as described below.

[1] A polyoxyethylene derivative represented by the formula (1):

(1)

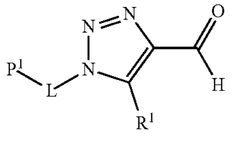

(in the formula (1), $R^1$ is a hydrogen atom or a substituent, $P^1$ is a group containing a polyoxyethylene chain having a number average molecular weight of 5,000 to 50,000, and L is a divalent spacer).

[2] The polyoxyethylene derivative of the aforementioned [1], wherein L is a divalent spacer represented by the formula (2):

(2)

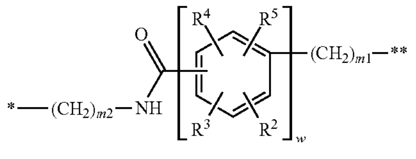

(in the formula (2), m1 is 0 or 1, m2 is an integer of 1 to 3, w is 1 or 2, $R^2$, $R^3$, $R^4$, and $R^5$ are each independently a hydrogen atom or a substituent,

* is a bonding point with $P^1$, and

** is a bonding point with N).

[3] The polyoxyethylene derivative of the aforementioned [2], wherein m1 is 0 and w is 1.

[4] A conjugate of the polyoxyethylene derivative of any one of the aforementioned [1] to [3] and a polypeptide.

[5] The conjugate of the aforementioned [4] which is represented by the formula (3):

(3)

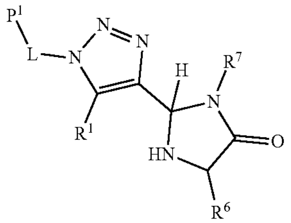

(in the formula (3), $R^1$ is a hydrogen atom or a substituent, $R^6$ is a side chain of an amino acid residue, $R^7$ is a group formed by removing —NH— from a terminal of an amino acid residue or a polypeptide chain, $P^1$ is a group containing a polyoxyethylene chain having a number average molecular weight of 5,000 to 50,000, and L is a divalent spacer).

Effect of the Invention

Using the releasable polyoxyethylene derivative of the present invention, a conjugate with a polypeptide capable of functioning as a biofunctional molecule, wherein the conjugate can be degraded over a long time under physiological conditions to release the aforementioned polypeptide, can be formed.

BRIEF DESCRIPTION OF THE DRAWINGS

FIG. 1 A graph showing the results obtained in Experimental Example 1 (degradability test).

DESCRIPTION OF EMBODIMENTS

The present invention is described in detail in the following.

The releasable polyoxyethylene derivative of the present invention can form a conjugate with a polypeptide, and the aforementioned conjugate can be degraded over a long time under physiological conditions to release the aforementioned polypeptide. In the present specification, the "physiological conditions" mean 35 to 40° C. and pH 7.0 to 8.0. In the present specification, that "a conjugate of a releasable polyoxyethylene derivative with a polypeptide is degraded over a long time under physiological conditions" means that the degradation half-life of the aforementioned conjugate under physiological conditions (i.e., the time for half of the aforementioned conjugate to degrade under physiological conditions to release the aforementioned polypeptide) is not less than one day. The aforementioned degradation half-life is preferably 1 to 30 days, more preferably 3 to 20 days, further preferably 3 to 10 days.

The protein (polypeptide) conjugate described in Example 18 of WO 2020/175680 could not achieve the aforementioned degradation half-life under physiological conditions. In contrast, the present inventors have found that the conjugate of the releasable polyoxyethylene derivative and polypeptide of the present invention (sometimes to be referred to as "the conjugate of the present invention" in the present specification) can achieve the aforementioned degradation half-life under physiological conditions.

The releasable polyoxyethylene derivative of the present invention is a polyoxyethylene derivative represented by the formula (1):

(1)

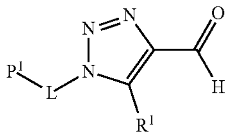

(in the formula (1), $R^1$ is a hydrogen atom or a substituent, $P^1$ is a group containing a polyoxyethylene chain having a number average molecular weight of 5,000 to 50,000, and L is a divalent spacer) (hereinafter sometimes to be referred to as "polyoxyethylene derivative (1)").

In the formula (1), $R^1$ is a hydrogen atom or a substituent.

Examples of the substituent for $R^1$ include halogen atom, alkyl group having 1 to 4 carbon atoms, halogenated alkyl group having 1 to 4 carbon atoms, alkoxy group having 1 to 4 carbon atoms, halogenated alkoxy group having 1 to 4 carbon atoms, acyl group having 2 to 5 carbon atoms, alkoxycarbonyl group having 2 to 5 carbon atoms, carbamoyl group having 2 to 5 carbon atoms, acyloxy group having 2 to 5 carbon atoms, acylamino group having 2 to 5 carbon atoms, alkoxycarbonylamino group having 2 to 5 carbon atoms, alkylsulfanyl group having 1 to 4 carbon atoms, alkylsulfonyl group having 1 to 4 carbon atoms, arylsulfonyl group having 6 to 10 carbon atoms, nitro group, trifluoromethyl group, cyano group, optionally-substituted phenyl group, and the like.

Examples of the substituent that a phenyl group optionally has include halogen atom, alkyl group having 1 to 4 carbon atoms, halogenated alkyl group having 1 to 4 carbon atoms, alkoxy group having 1 to 4 carbon atoms, halogenated alkoxy group having 1 to 4 carbon atoms, acyl group having 2 to 5 carbon atoms, alkoxycarbonyl group having 2 to 5 carbon atoms, carbamoyl group having 2 to 5 carbon atoms, acyloxy group having 2 to 5 carbon atoms, acylamino group having 2 to 5 carbon atoms, alkoxycarbonylamino group having 2 to 5 carbon atoms, alkylsulfanyl group having 1 to 4 carbon atoms, alkylsulfonyl group having 1 to 4 carbon atoms, arylsulfonyl group having 6 to 10 carbon atoms, nitro group, trifluoromethyl group, cyano group, and the like.

$R^1$ is

- preferably a hydrogen atom, a halogen atom, an alkyl group having 1 to 4 carbon atoms, a halogenated alkyl group having 1 to 4 carbon atoms, an alkoxy group having 1 to 4 carbon atoms, a halogenated alkoxy group having 1 to 4 carbon atoms, or an optionally-substituted phenyl group,
- more preferably a hydrogen atom, a halogen atom, an alkyl group having 1 to 4 carbon atoms, or a halogenated alkyl group having 1 to 4 carbon atoms, or a phenyl group optionally substituted by substituent (s) selected from the group consisting of a halogen atom, an alkyl group having 1 to 4 carbon atoms, an alkoxy group having 1 to 4 carbon atoms, and a nitro group,
- further preferably a hydrogen atom, a methyl group, a difluoromethyl group, a trifluoromethyl group, a phenyl group, a fluorophenyl group (e.g., 2-fluorophenyl group), a methoxyphenyl group (e.g., 4-methoxyphenyl group), or a nitrophenyl group (e.g., 4-nitrophenyl group).

In the formula (1), $P^1$ is a group containing a polyoxyethylene chain having a number average molecular weight of 5,000 to 50,000. The number average molecular weight of the polyoxyethylene chain of $P^1$ can be calculated by subtracting the molecular weight derived from molecules other than the polyoxyethylene chain from the number average molecular weight determined by size-exclusion chromatography, mass spectrometry method, or the like of the polyoxyethylene derivative as the raw material. For example, when $P^1$ is represented by the below-mentioned formula (p1), it can be calculated by subtracting the molecular weight of the alkoxy group represented by $X^1$—O— at the terminal and the atomic weight of the hydrogen atom from the number average molecular weight of $X^1$—O—$(CH_2CH_2O)_{n1}$—H as the starting material. When $P^1$ has a plurality of polyoxyethylene chains, the "number average molecular weight of the polyoxyethylene chain" in the present specification means a total number average molecular weight of the plurality of polyoxyethylene chains.

The number average molecular weight of the polyoxyethylene chain of $P^1$ is preferably 10,000 to 50,000, more preferably 15,000 to 50,000, further preferably 15,000 to 45,000, from the aspect of extension of the half-life in blood of polypeptide.

$P^1$ is preferably a group represented by the formula (p1):

$$X^1—O—(CH_2CH_2O)_{n1}—*** \quad (p1)$$

(in the formula (p1), $X^1$ is an alkyl group having 1 to 24 carbon atoms, n1 is 114 to 1,136, and

*** is a bonding point with L)

or a group represented by the formula (p2):

(p2)

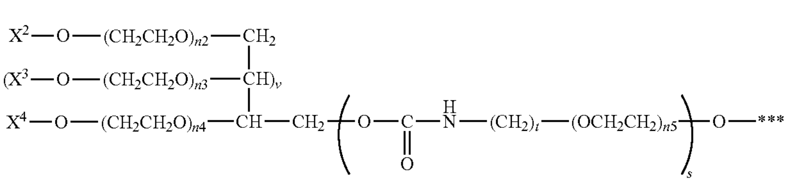

(in the formula (p2)

$X^2$ to $X^4$ are each independently an alkyl group having 1 to 24 carbon atoms, n2 to n5 are each independently a number of 57 to 568, a total of n2 to n4 is a number of 114 to 1, 136, s is 0 or 1, t is 2 or 3, v is 0 or 2, and

*** is a bonding point with L).

In the formulas (p1) and (p2), n1 to n5 may be decimals, since each represents the number of repeats of the oxyethylene units. n1 in the formula (p1) is preferably a number of 204 to 1023, more preferably a number of 409 to 1023. n2 to n4 in the formula (p2) are each independently, preferably a number of 102 to 568, more preferably a number of 102 to 511, further preferably a number of 204 to 511, and the total of these is preferably a number of 114 to 1023, more preferably a number of 204 to 1023, further preferably a number of 409 to 1023.

In the formula (p2), that s is 0 means that $(O—CO—NH—(CH_2)_t—(OCH_2CH_2)_{n5})_s$ is not present, and the moiety of $—(O—CO—NH—(CH_2)_t—(OCH_2CH_2)_{m5})_s—$ is a single bond. s is preferably 0.

In the formula (p2), that v is 0 means that $X^3—O—(OCH_2CH_2O)_{n3}—CH$ is not present, and the moiety of —(CH)— to which $X^3—O—(OCH_2CH_2O)_{n3}—$ is bonded is a single bond. v is preferably 0.

Examples of the alkyl group having 1 to 24 carbon atoms for $X^1$ to $X^4$ include methyl group, ethyl group, propyl group, isopropyl group, butyl group, tert-butyl group, pentyl group, isopentyl group, hexyl group, heptyl group, 2-ethylhexyl group, octyl group, nonyl group, decyl group, undecyl group, dodecyl group, tridecyl group, tetradecyl group, pentadecyl group, hexadecyl group, heptadecyl group, octadecyl group, nonadecyl group, eicosyl group, heneicosyl group, docosyl group, tricosyl group, tetracosyl group, and the like. Preferably, $X^1$ to $X^4$ are each independently an alkyl group having 1 to 10 carbon atoms, more preferably a methyl group or an ethyl group, further preferably a methyl group.

In the group represented by the formula (p1), $X^1$ is preferably an alkyl group having 1 to 24 carbon atoms, and n1 is preferably a number of 204 to 1023, $X^1$ is more preferably an alkyl group having 1 to 10 carbon atoms, and n1 is more preferably a number of 204 to 1023, $X^1$ is further preferably a methyl group or an ethyl group, and n1 is further preferably a number of 409 to 1023, $X^1$ is particularly preferably a methyl group, and n1 is particularly preferably a number of 409 to 1023.

In the group represented by the formula (p2), v is preferably 0, s is preferably 0, $X^2$ and $X^4$ are preferably each independently an alkyl group having 1 to 24 carbon atoms, n2 and n4 are preferably each independently a number of 57 to 568, and a total of n2 and n4 is preferably a number of 114 to 1023, v is more preferably 0, s is more preferably 0, $X^2$ and $X^4$ are more preferably each independently an alkyl group having 1 to 10 carbon atoms, n2 and n4 are more preferably each independently a number of 102 to 568, and a total of n2 and n4 is more preferably a number of 204 to 1023, v is further preferably 0, s is further preferably 0, $X^2$ and $X^4$ are further preferably each independently a methyl group or an ethyl group, n2 and n4 are further preferably each independently a number of 102 to 511, and a total of n2 and n4 is further preferably a number of 409 to 1023, v is particularly preferably 0, s is particularly preferably 0, $X^2$ and $X^4$ are each particularly preferably a methyl group, n2 and n4 are particularly preferably each independently a number of 204 to 511, and a total of n2 and n4 is particularly preferably a number of 409 to 1023.

In the formula (1), L is a divalent spacer (specifically, a divalent spacer connecting $P^1$ and triazole ring). Examples of the divalent spacer for L include (i) a combination of an optionally-substituted alkylene group having 1 to 24 carbon atoms and at least one selected from the group consisting of an amide bond (—NH—CO— or —CO—NH—), an ether bond (—O—), a thioether bond (—S—), a urethane bond (—NH—CO—O— or —O—CO—NH—), an imino group (—NH—), a carbonyl group (—CO—), and a urea bond (—NH—CO—NH—), and (ii) a combination of an optionally-substituted phenylene group (-Ph-), an optionally-substituted alkylene group having 1 to 24 carbon atoms, and at least one selected from the group consisting of an amide bond (—NH—CO— or —CO—NH—), an ether bond (—O—), a thioether bond (—S—), a urethane bond (—NH—CO—O— or —O—CO—NH—), an imino group (—NH—), a carbonyl group (—CO—), and a urea bond (—NH—CO—NH—).

L in the aforementioned (i) or (ii) may have two or more of each of the "at least one selected from the group consisting of an amide bond (—NH—CO— or —CO—NH—), an ether bond (—O—), a thioether bond (—S—), a urethane bond (—NH—CO—O— or —O—CO—NH—), an imino group (—NH—), a carbonyl group (—CO—), and a urea bond (—NH—CO—NH—)", the "optionally-substituted alkylene group having 1 to 24 carbon atoms", and the "optionally-substituted phenylene group (-Ph-)". For example, L in the aforementioned (i) may have a biphenylene structure (-Ph-Ph-) in which two "optionally-substituted phenylene groups (-Ph-)" are connected.

L is preferably a divalent spacer represented by the formula (2):

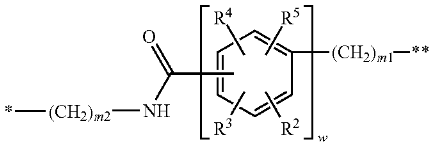

(2)

(in the formula (2), m1 is 0 or 1, m2 is an integer of 1 to 3, w is 1 or 2, $R^2$, $R^3$, $R^4$, and $R^5$ are each independently a hydrogen atom or a substituent,

* is a bonding point with $P^1$, and

** is a bonding point with N).

In the formula (2), m1 and m2 are each the number of repeats of the methylene unit. m1 is 0 or 1, preferably 0. That m1 is 0 here means that $—(CH_2)_{m1}—$ is a single bond. m2 is an integer of 1 to 3, preferably 3.

In the formula (2), w is the number of repeats of the optionally-substituted phenylene unit. w is 1 or 2, preferably 1.

In the formula (2), m1 is preferably 0, and w is preferably 1.

In the formula (2), $R^2$ to $R^5$ are each independently a hydrogen atom or a substituent.

When w is 2, $R^2$ in the number of two may be the same or different, $R^3$ in the number of two may be the same or different, $R^4$ in the number of two may be the same or different, and $R^5$ in the number of two may be the same or different.

Examples of the substituent for $R^2$ to $R^5$ include halogen atom, alkyl group having 1 to 4 carbon atoms, halogenated alkyl group having 1 to 4 carbon atoms, alkoxy group having 1 to 4 carbon atoms, halogenated alkoxy group having 1 to 4 carbon atoms, acyl group having 2 to 5 carbon atoms, alkoxycarbonyl group having 2 to 5 carbon atoms, carbamoyl group having 2 to 5 carbon atoms, acyloxy group having 2 to 5 carbon atoms, acylamino group having 2 to 5 carbon atoms, alkoxycarbonylamino group having 2 to 5 carbon atoms, alkylsulfanyl group having 1 to 4 carbon atoms, alkylsulfonyl group having 1 to 4 carbon atoms, arylsulfonyl group having 6 to 10 carbon atoms, nitro group, trifluoromethyl group, a cyano group, and the like.

$R^2$ to $R^5$ are preferably each independently a hydrogen atom, an alkyl group having 1 to 4 carbon atoms, an alkoxy group having 1 to 4 carbon atoms, or a nitro group, more preferably a hydrogen atom, an alkoxy group having 1 to 4 carbon atoms, or a nitro group, further preferably a hydrogen atom, a methoxy group, or a nitro group.

In the formula (2), m1 is preferably 0 or 1, m2 is preferably an integer of 1 to 3, w is preferably 1 or 2, and $R^2$ to $R^5$ are preferably each independently a hydrogen atom, an alkyl group having 1 to 4 carbon atoms, an alkoxy group having 1 to 4 carbon atoms, or a nitro group, m1 is more preferably 0 or 1, m2 is more preferably an integer of 1 to 3, w is more preferably 1 or 2, and $R^2$ to $R^5$ are more preferably each independently a hydrogen atom, an alkoxy group having 1 to 4 carbon atoms, or a nitro group, m1 is further preferably 0 or 1, m2 is further preferably an integer of 1 to 3, w is further preferably 1 or 2, and $R^2$ to $R^5$ are further preferably each independently a hydrogen atom, an alkoxy group having 1 to 4 carbon atoms, or a nitro group, m1 is particularly preferably 0, m2 is particularly preferably 3, w is particularly preferably 1, and $R^2$ to $R^5$ are particularly preferably each independently a hydrogen atom, a methoxy group, or a nitro group.

As L represented by the formula (2), a divalent spacer represented by the formula (2a):

(2a)

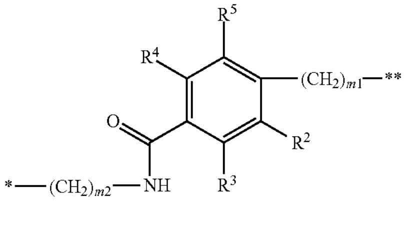

(in the formula (2a), the symbols are as defined above), a divalent spacer represented by the formula (2b):

(2b)

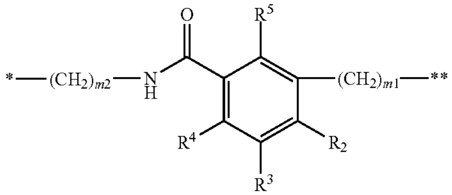

(in the formula (2b), the symbols are as defined above), or a divalent spacer represented by the formula (2c):

(2c)

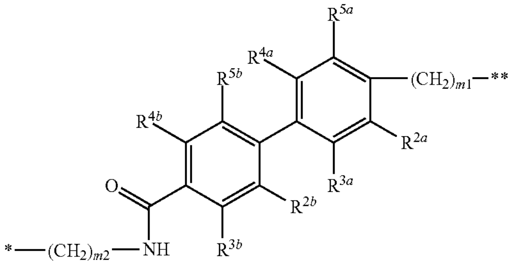

(in the formula (2c), $R^{2a}$ to $R^{5a}$ and $R^{2b}$ to $R^{5b}$ are each independently a hydrogen atom or a substituent, and other symbols are as defined above) is preferred. The substituents for $R^{2a}$ to $R^{5a}$ and $R^{2b}$ to $R^{5b}$ are the same as those for the aforementioned $R^2$ to $R^5$.

In the formula (2a), m1 is preferably 0 or 1, m2 is preferably an integer of 1 to 3, and $R^2$ to $R^5$ are preferably each independently a hydrogen atom, an alkyl group having 1 to 4 carbon atoms, an alkoxy group having 1 to 4 carbon atoms, or a nitro group, m1 is more preferably 0 or 1, m2 is more preferably an integer of 1 to 3, and $R^2$ to $R^5$ are more preferably each independently a hydrogen atom, an alkoxy group having 1 to 4 carbon atoms, or a nitro group, m1 is further preferably 0 or 1, m2 is further preferably an integer of 1 to 3, and $R^2$ to $R^5$ are further preferably each independently a hydrogen atom, an alkoxy group having 1 to 4 carbon atoms, or a nitro group, m1 is particularly preferably 0, m2 is particularly preferably an integer of 1 to 3, and $R^2$ to $R^5$ are particularly preferably each independently a hydrogen atom, an alkoxy group having 1 to 4 carbon atoms, or a nitro group, m1 is most preferably 0, m2 is most preferably 3, $R^2$ is most preferably a hydrogen atom or a methoxy group, and $R^3$ to $R^5$ are each most preferably a hydrogen atom.

In the formula (2b), m1 is preferably 0 or 1, m2 is preferably an integer of 1 to 3, and $R^2$ to $R^5$ are preferably each independently a hydrogen atom, an alkyl group having 1 to 4 carbon atoms, an alkoxy group having 1 to 4 carbon atoms, or a nitro group, m1 is more preferably 0 or 1, m2 is more preferably an integer of 1 to 3, and $R^2$ to $R^5$ are more preferably each independently a hydrogen atom, an alkoxy group having 1 to 4 carbon atoms, or a nitro group, m1 is further preferably 0 or 1, m2 is further preferably an integer of 1 to 3, and $R^2$ to $R^5$ are further preferably each independently a hydrogen atom, an alkoxy group having 1 to 4 carbon atoms, or a nitro group, m1 is particularly preferably 0, m2 is particularly preferably an integer of 1 to 3, and $R^2$ to $R^5$ are particularly preferably each independently a hydrogen atom, an alkoxy group having 1 to 4 carbon atoms, or a nitro group, m1 is most preferably 0, m2 is most preferably 3, and $R^2$ and $R^4$ are most preferably each independently a hydrogen atom, a methoxy group, or a nitro group, and $R^3$ and $R^5$ are each most preferably a hydrogen atom.

In the formula (2c), m1 is preferably 0 or 1, m2 is preferably an integer of 1 to 3, and $R^{2a}$ to $R^{5a}$ and $R^{2b}$ to $R^{5b}$ are preferably each independently a hydrogen atom, an alkyl group having 1 to 4 carbon atoms, an alkoxy group having 1 to 4 carbon atoms, or a nitro group, m1 is more preferably 0 or 1, m2 is more preferably an integer of 1 to 3, and $R^{2a}$ to $R^{5a}$ and $R^{2b}$ to $R^{5b}$ are more preferably each independently a hydrogen atom, an alkoxy group having 1 to 4 carbon atoms, or a nitro group, m1 is further preferably 0 or 1, m2 is further preferably an integer of 1 to 3, and $R^{2a}$ to $R^{5a}$ and $R^{2b}$ to $R^{5b}$ are further preferably each independently a hydrogen atom, an alkoxy group having 1 to 4 carbon atoms, or a nitro group, m1 is particularly preferably 0, m2 is particularly preferably an integer of 1 to 3, and $R^{2a}$ to $R^{5a}$ and $R^{2b}$ to $R^{5b}$ are particularly preferably each independently a hydrogen atom, an alkoxy group having 1 to 4 carbon atoms, or a nitro group, m1 is most preferably 0, m2 is most preferably 3, and $R^{2a}$ to $R^{5a}$ and $R^{2b}$ to $R^{5b}$ are each most preferably a hydrogen atom.

Preferred examples of the polyoxyethylene derivative (1) of the present invention include the following polyoxyethylene derivative (1-1) to polyoxyethylene derivative (1-6).

<Polyoxyethylene derivative (1-1)>

A polyoxyethylene derivative wherein $R^1$ is a hydrogen atom, a halogen atom, an alkyl group having 1 to 4 carbon atoms, a halogenated alkyl group having 1 to 4 carbon atoms, an alkoxy group having 1 to 4 carbon atoms, a halogenated alkoxy group having 1 to 4 carbon atoms, or an optionally-substituted phenyl group;

$P^1$ is (i) a group represented by the formula (p1) (in the formula (p1), $X^1$ is an alkyl group having 1 to 24 carbon atoms, and n1 is a number of 114 to 1,136), or (ii) a group represented by the formula (p2) (in the formula (p2), v is 0, s is 0, $X^2$ and $X^4$ are each independently an alkyl group having 1 to 24 carbon atoms, n2 and n4 are each independently a number of 57 to 568, and a total of n2 and n4 is a number of 114 to 1136); and L is (i) a divalent spacer represented by the formula (2a) (in the formula (2a), m1 is 0 or 1, m2 is an integer of 1 to 3, and $R^2$ to $R^5$ are each independently a hydrogen atom, an alkyl group having 1 to 4 carbon atoms, an alkoxy group having 1 to 4 carbon atoms, or a nitro group), (ii) a divalent spacer represented by the formula (2b) (in the formula (2b), m1 is 0 or 1, m2 is an integer of 1 to 3, and $R^2$ to $R^5$ are each independently a hydrogen atom, an alkyl group having 1 to 4 carbon atoms, an alkoxy group having 1 to 4 carbon atoms, or a nitro group), or (iii) a divalent spacer represented by the formula (2c) (in the formula (2c), m1 is 0 or 1, m2 is an integer of 1 to 3, $R^{2a}$ to $R^{5a}$ and $R^{2b}$ to $R^{5b}$ are each independently a hydrogen atom, an alkyl group having 1 to 4 carbon atoms, an alkoxy group having 1 to 4 carbon atoms, or a nitro group).

In the above-mentioned embodiments, *, , and * in the formula (p1), the formula (p2), and the formula (2a) to the formula (2c) are as defined above.

<Polyoxyethylene derivative (1-2)>

A polyoxyethylene derivative wherein $R^1$ is a hydrogen atom, a halogen atom, an alkyl group having 1 to 4 carbon atoms, or a halogenated alkyl group having 1 to 4 carbon atoms, or a phenyl group optionally substituted by substituent (s) selected from the group consisting of a halogen atom, an alkyl group having 1 to 4 carbon atoms, an alkoxy group having 1 to 4 carbon atoms, and a nitro group;

$P^1$ is (i) a group represented by the formula (p1) (in the formula (p1), $X^1$ is an alkyl group having 1 to 10 carbon atoms, and n1 is a number of 204 to 1023), or (ii) a group represented by the formula (p2) (in the formula (p2), v is 0, s is 0, $X^2$ and $X^4$ are each independently an alkyl group having 1 to 10 carbon atoms, n2 and n4 are each independently a number of 102 to 568, and a total of n2 and n4 is a number of 204 to 1023); and L is (i) a divalent spacer represented by the formula (2a) (in the formula (2a), m1 is 0 or 1, m2 is an integer of 1 to 3, and $R^2$ to $R^5$ are each independently a hydrogen atom, an alkoxy group having 1 to 4 carbon atoms, or a nitro group), (ii) a divalent spacer represented by the formula (2b) (in the formula (2b), m1 is 0 or 1, m2 is an integer of 1 to 3, and $R^2$ to $R^5$ are each independently a hydrogen atom, an alkoxy group having 1 to 4 carbon atoms, or a nitro group), or (iii) a divalent spacer represented by the formula (2c) (in the formula (2c), m1 is 0 or 1, m2 is an integer of 1 to 3, and $R^{2a}$ to $R^{5a}$ and $R^{2b}$ to $R^{5b}$ are each independently a hydrogen atom, an alkoxy group having 1 to 4 carbon atoms, or a nitro group).

In the above-mentioned embodiments, *, , and * in the formula (p1), the formula (p2), and the formula (2a) to the formula (2c) are as defined above.

<Polyoxyethylene derivative (1-3)>

A polyoxyethylene derivative wherein $R^1$ is a hydrogen atom, a methyl group, a difluoromethyl group, a trifluoromethyl group, a phenyl group, a fluorophenyl group (e.g., 2-fluorophenyl group), a methoxyphenyl group (e.g., 4-methoxyphenyl group), or a nitrophenyl group (e.g., 4-nitrophenyl group);

$P^1$ is (i) a group represented by the formula (p1) (in the formula (p1), $X^1$ is a methyl group or an ethyl group, and n1 is a number of 409 to 1023), or (ii) a group represented by the formula (p2) (in the formula (p2), v is 0, s is 0, $X^2$ and $X^4$ are each independently a methyl group or an ethyl group, and n2 and n4 are each independently a number of 204 to 511, and a total of n2 and n4 is a number of 409 to 1023); and L is (i) a divalent spacer represented by the formula (2a) (in the formula (2a), m1 is 0 or 1, m2 is an integer of 1 to 3, and $R^2$ to $R^5$ are each independently a hydrogen atom, an alkoxy group having 1 to 4 carbon atoms, or a nitro group), (ii) a divalent spacer represented by the formula (2b) (in the formula (2b), m1 is 0 or 1, m2 is an integer of 1 to 3, and $R^2$ to $R^5$ are each independently a hydrogen atom, an alkoxy group having 1 to 4 carbon atoms, or a nitro group), or (iii) a divalent spacer represented by the formula (2c) (in the formula (2c), m1 is 0 or 1, m2 is an integer of 1 to 3, and $R^{2a}$ to $R^{5a}$ and $R^{2b}$ to $R^{5b}$ are each independently a hydrogen atom, an alkoxy group having 1 to 4 carbon atoms, or a nitro group).

In the above-mentioned embodiments, *, , and * in the formula (p1), the formula (p2), and the formula (2a) to the formula (2c) are as defined above.

<Polyoxyethylene derivative (1-4)>

A polyoxyethylene derivative wherein $R^1$ is a hydrogen atom, a methyl group, a difluoromethyl group, a trifluoromethyl group, a phenyl group, a fluorophenyl group (e.g., 2-fluorophenyl group), a methoxyphenyl group (e.g., 4-methoxyphenyl group), or a nitrophenyl group (e.g., 4-nitrophenyl group);

$P^1$ is (i) a group represented by the formula (p1) (in the formula (p1), $X^1$ is a methyl group, and n1 is a number of 409 to 1023), or (ii) a group represented by the formula (p2) (in the formula (p2), v is 0, s is 0, $X^2$ and $X^4$ are each a methyl group, and n2 and n4 are each independently a number of 204 to 511, and a total of n2 and n4 is a number of 409 to 1023); and L is (i) a divalent spacer represented by the formula (2a) (in the formula (2a), m1 is 0, m2 is an integer of 1 to 3, and $R^2$ to $R^5$ are each independently a hydrogen atom, an alkoxy group having 1 to 4 carbon atoms, or a nitro group), (ii) a divalent spacer represented by the formula (2b) (in the formula (2b), m1 is 0, m2 is an integer of 1 to 3, and $R^2$ to $R^5$ are each independently a hydrogen atom, an alkoxy group having 1 to 4 carbon atoms, or a nitro group), or (iii) a divalent spacer represented by the formula (2c) (in the formula (2c), m1 is 0, m2 is an integer of 1 to 3, and $R^{2a}$ to $R^{5a}$ and $R^{2b}$ to $R^{5b}$ are each independently a hydrogen atom, an alkoxy group having 1 to 4 carbon atoms, or a nitro group).

In the above-mentioned embodiments, *, , and * in the formula (p1), the formula (p2), and the formula (2a) to the formula (2c) are as defined above.

<Polyoxyethylene derivative (1-5)>

A polyoxyethylene derivative wherein $R^1$ is a hydrogen atom, a methyl group, a difluoromethyl group, a trifluoromethyl group, a phenyl group, a fluorophenyl group (e.g., 2-fluorophenyl group), a methoxyphenyl group (e.g., 4-methoxyphenyl group), or a nitrophenyl group (e.g., 4-nitrophenyl group);

$P^1$ is (i) a group represented by the formula (p1) (in the formula (p1), $X^1$ is a methyl group, and n1 is a number of 409 to 1023), or (ii) a group represented by the formula (p2) (in the formula (p2), v is 0, s is 0, $X^2$ and $X^4$ are each a methyl group, and n2 and n4 are each independently a number of 204 to 511, and the total of n2 and n4 is a number of 409 to 1023); and L is (i) a divalent spacer represented by the formula (2a) (in the formula (2a), m1 is 0, m2 is an integer of 1 to 3, $R^2$ is a hydrogen atom or a methoxy group, and $R^3$ to $R^5$ are each a hydrogen atom), (ii) a divalent spacer represented by the formula (2b) (in the formula (2b), m1 is 0, m2 is an integer of 1 to 3, and $R^2$ and $R^4$ are each independently a hydrogen atom, a methoxy group, or a nitro group, and $R^3$ and $R^5$ are each a hydrogen atom), or (iii) a divalent spacer represented by the formula (2c) (in the formula (2c), m1 is 0, m2 is an integer of 1 to 3, and $R^{2a}$ to $R^{5a}$ and $R^{2b}$ to $R^{5b}$ are each a hydrogen atom).

In the above-mentioned embodiments, *, , and * in the formula (p1), the formula (p2), and the formula (2a) to the formula (2c) are as defined above.

<Polyoxyethylene derivative (1-6)>

A polyoxyethylene derivative wherein $R^1$ is a hydrogen atom, a methyl group, a difluoromethyl group, a trifluoromethyl group, a phenyl group, a fluorophenyl group (e.g., 2-fluorophenyl group), a methoxyphenyl group (e.g., 4-methoxyphenyl group), or a nitrophenyl group (e.g., 4-nitrophenyl group);

$P^1$ is (i) a group represented by the formula (p1) (in the formula (p1), $X^1$ is a methyl group, and n1 is a number of 409 to 1023), or (ii) a group represented by the formula (p2) (in the formula (p2), v is 0, s is 0, $X^2$ and $X^4$ are each a methyl group, and n2 and n4 are each independently a number of 204 to 511, and the total of n2 and n4 is a number of 409 to 1023); and L is (i) a divalent spacer represented by the formula (2a) (in the formula (2a), m1 is 0, m2 is 3, $R^2$ is a hydrogen atom or a methoxy group, and $R^3$ to $R^5$ are each a hydrogen atom), or (ii) a divalent spacer represented by the formula (2b) (in the formula (2b), m1 is 0, m2 is 3, and $R^2$ and $R^4$ are each independently a hydrogen atom, a methoxy group, or a nitro group, and $R^3$ and $R^5$ are each a hydrogen atom).

In the above-mentioned embodiments, *, , and * in the formula (p1), the formula (p2), the formula (2a), and the formula (2b) are as defined above.

The present invention also provides a conjugate of polyoxyethylene derivative (1) and polypeptide (sometimes to be referred to as "the conjugate of the present invention" in the present specification). In the present specification, the "polypeptide" also includes oligopeptides such as dipeptide, tripeptide, and the like.

The conjugate of the present invention is preferably a conjugate represented by the formula (3):

(3)

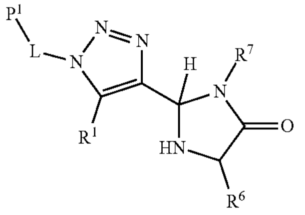

(in the formula (3), $R^6$ is a side chain of an amino acid residue, $R^7$ is a group formed by removing —NH— from a terminal of an amino acid residue or a polypeptide chain, and other symbols are as defined above).

In the formula (3), $R^6$ is a hydrogen atom or a side chain of an amino acid residue. As is well known in the field of amino acids, the amino acid residue means a divalent group obtained by removing H from $—NH_2$ and removing the OH from —COOH of an amino acid. The side chain of an amino acid residue is a side chain that the amino acid that forms an amino acid residue has. The amino acid for forming the amino acid residue is not particularly limited, and includes, for example, glycine, alanine, serine, threonine, asparagine, glutamine, aspartic acid, glutamic acid, lysine, arginine, histidine, valine, leucine, isoleucine, tyrosine, phenylalanine, tryptophan, proline, methionine, and cysteine. Note that when the amino acid residue is a glycine residue, the "side chain of the amino acid residue" for $R^6$ is a hydrogen atom.

$R^7$ in the formula (3) is a group obtained by removing —NH— from a terminal of an amino acid residue or a polypeptide chain. The —NH— is used to form a nitrogen-containing ring in the formula (3).

The polypeptide that binds to polyoxyethylene derivative (1) is preferably a biofunctional substance. The "polypeptide as a biofunctional substance" here means a polypeptide involved in the diagnosis, healing, mitigation, treatment, or prophylaxis of diseases in human or other animals. Examples of the polypeptide as a biofunctional substance include cytokine, hormone, antibody, enzyme, growth factor, blood coagulation factor, and the like.

Examples of the cytokine include interferon type I, type II, and type III that regulate immunity, interleukin, tumor necrosis factor, receptor antagonist thereof, and the like.

Examples of the hormone include calcitonin, insulin, analogue thereof, exenatide thereof, GLP-1, somatostatin, human growth hormone, and the like.

Examples of the antibody include full length antibody, Fab, svFV, and the like.

Examples of the enzyme include ribonuclease (RNase), superoxide dismutase, uricase, and the like.

Examples of the growth factor include erythropoietin which is a hemopoietic factor, granulocyte colony stimulating factor (GCSF) which is a stimulating factor, and the like.

Examples of the blood coagulation factor include factor V, factor VII, factor VIII, factor IX, factor X, factor XII, and the like.

Preferred examples of polypeptides include RNase, interferon, interleukin, erythropoietin, GCSF, factor VIII, factor IX, human growth hormone, antibody fragment, insulin, bivalirudin, teriparatide, exenatide, enfuvirtide, degarelix, mifamurtide, nesiritide, goserelin, glatiramer, octreotide, lanreotide, icatibant, dicotinide, pramlintide, romiplostim, calcitonin, oxytocin, leuprorelin, glucagon, and the like. Among these, RNase, human growth hormone, interferon, GCSF, erythropoietin, antibody fragment (particularly Fab), insulin, exenatide, and calcitonin (particularly salmon calcitonin) are more preferred.

The conjugate of polyoxyethylene derivative (1) and polypeptide of the present invention can be degraded over a long time under physiological conditions to release the aforementioned polypeptide. The polyoxyethylene derivative (1) of the present invention is preferably used to form such conjugate. In addition, the conjugate of the present invention is preferably used for degradation over a long time under physiological conditions to release the aforementioned polypeptide.

EXAMPLE

The present invention is explained in more detail in the following based on Examples and Experimental Examples; however, the present invention is not limited to the following Examples and Experimental Examples.

$^1$H-NMR in the following Examples was measured using JNM-ECP400 or JNM-ECA600 manufactured by JEOL Datum Co., Ltd. A φ5 mm tube was used for the measurement, and $D_2O$ containing sodium 3-(trimethylsilyl)-1-propanesulfonate as an internal standard or de-DMSO containing tetramethylsilane (TMS) as an internal standard was used as the deuterated solvent.

[Example 1] Synthesis of Compound (6) (mPEG (20k)-BzTA4C) Represented by the Following Formula (in the Following Formula, n is about 455)

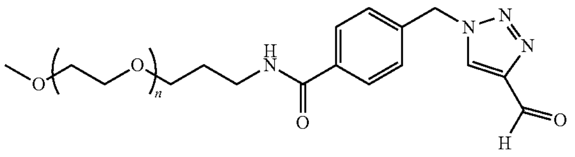

4-((4-Formyl-1H-1, 2, 3-triazol-1-yl)methyl)benzoic acid (15.1 mg, 0.0656 mmol) synthesized with reference to WO 2020/175680 and 4-(4,6-dimethoxy-1,3,5-triazin-2-yl)-4-methylmorpholinium chloride (n hydrate) (DMT-MM) (45.4 mg, 0.1313 mmol) were dissolved in acetonitrile (4.5 g) and the mixture was stirred for 1 hr. Thereafter, SUNBRIGHT MEPA-20T manufactured by NOF CORPORATION (number average molecular weight: 19,729) (700 mg, 0.035 mmol) was added, and the mixture was reacted under a nitrogen atmosphere at room temperature for 3 hr. After the reaction, toluene (100 g) was added, and the mixture was stirred for 5 min. After stirring, hexane (50 g) was added and the mixture was stirred at room temperature for min to precipitate crystals. The crystals were collected by suction filtration and dried to obtain compound (6) (mPEG (20k)-BzTA4C) (459 mg).

$^1$H-NMR ($d_6$-DMSO); 1.74 ppm (m, 2H, $—(CH_2CH_2O)_n—CH_2—\underline{CH_2}—CH_2—$), 3.24 ppm (s, 3H, $\underline{CH_3}—O—(CH_2CH_2O)_n—$), 3.64 ppm (m, about 1, 800H, $CH_3—O—\underline{(CH_2CH_2O)_n}—$), 5.75 ppm (s, 2H, $—NH—CO—(C_6H_4)—\underline{CH_2}—$), 7.4-7.8 ppm (m, 4H, $—NH—CO—\underline{(C_6H_4)}—CH_2—$), 8.63 ppm (m, 1H, $—\underline{NH}—CO—(C_6H_4)—$), 9.03 ppm (s, 1H, —($C_6H_4$)—$CH_2$— ($C_2HN_3$)—CHO), 10.04 ppm (s, 1H, ($C_6H_4$)—$CH_2$—($C_2HN_3$)—CHO)

[Example 2] Synthesis of Compound (7) (mPEG (10k)-BzTA4C) Represented by the Following Formula (in the Following Formula, n is about 227)

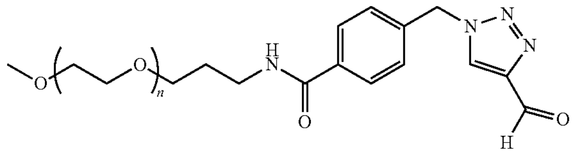

4-((4-Formyl-1H-1, 2, 3-triazol-1-yl)methyl)benzoic acid (32.4 mg, 0.14 mmol) synthesized with reference to wo 2020/175680 and DMT-MM (96.9 mg, 0.28 mmol) were dissolved in acetonitrile (4.8 g) and the mixture was stirred for 1 hr. Thereafter, SUNBRIGHT MEPA-10T manufactured by NOF CORPORATION (number average molecular weight: 10,386) (800 mg, 0.08 mmol) was added, and the mixture was reacted under a nitrogen atmosphere at room temperature for 3 hr. After the reaction, a concentrated solution obtained by concentration was diluted with toluene (100 g) and stirred under a nitrogen atmosphere at room temperature for 5 min. After stirring, hexane (50 g) was added to precipitate crystals. The crystals were collected by suction filtration, 2-propanol (150 g) was added, and the mixture was stirred under a nitrogen atmosphere at room temperature for 15 min. After stirring, the crystals were collected by suction filtration and dried to obtain compound (7) (mPEG (10k)-BzTA4C) (693 mg).

$^1$H-NMR (de-DMSO); 1.74 ppm (m, 2H, —($CH_2CH_2O$)$_n$—$CH_2$—$CH_2$—$CH_2$—), 3.24 ppm (s, 3H, $CH_3$—O—($CH_2CH_2O$)$_n$—), 3.64 ppm (m, about 900H, $CH_3$—O—($CH_2CH_2O$)$_n$—), 5.75 ppm (s, 2H, —NH—CO—($C_6H_4$)—$CH_2$—), 7.4-7.8 ppm (m, 4H, —NH—CO—($C_6H_4$)—$CH_2$—), 8.63 ppm (m, 1H, —NH—CO—($C_6H_4$)—), 9.03 ppm (s, 1H, —($C_6H_4$)—$CH_2$—($C_2HN_3$)—CHO), 10.04 ppm (s, 1H, ($C_6H_4$)—$CH_2$—($C_2HN_3$)—CHO)

[Example 3] Synthesis of Compound (8) (mPEG (20k)-PhTA4C (4CB)) Represented by the Following Formula (in the Following Formula, n is about 455)

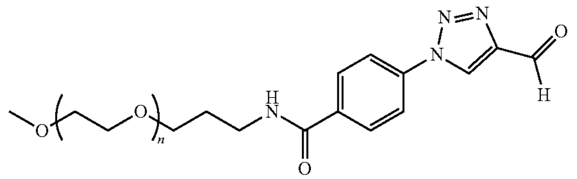

[Example 3-1] Synthesis of Compound (9) (mPEG (20k)-Ph-Azide (4CB)) Represented by the Following Formula (in the Following Formula, n is about 455)

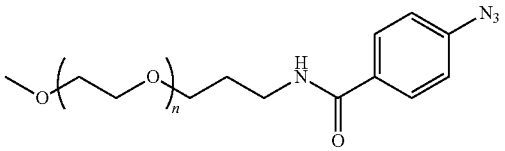

SUNBRIGHT MEPA-20T manufactured by NOF CORPORATION (5.0 g, 0.25 mmol) was dissolved in acetonitrile (20 g). 4-Azidobenzoic acid (61.2 mg, 0.375 mmol), N, N-diisopropyl ethylamine (DIPEA) (63.8 μL, 0.375 mmol), and DMT-MM (259.4 mg, 0.75 mmol) were added, and the mixture was reacted under a nitrogen atmosphere at room temperature for 3 hr. After the reaction, the mixture was concentrated, the obtained concentrated solution was diluted with toluene (100 g) and stirred under a nitrogen atmosphere at room temperature for 5 min. Thereafter, hexane (50 g) was added to precipitate crystals. The crystals were collected by suction filtration, 2-propanol (150 g) was added under a nitrogen atmosphere, and the mixture was stirred at room temperature for 15 min. After stirring, the crystals were collected by suction filtration and dried to obtain compound (9) (mPEG (20k)-Ph-Azide) (4.8 g).

[Example 3-2] Synthesis of Compound (8) (mPEG (20k)-PhTA4C (4CB))

Compound (9) (3.0 g, 0.15 mmol) obtained in Example 3-1 and tert-butyl-p-cresol (BHT) (3.0 mg) were dissolved in a mixed solution of 100 mM copper (II) sulfate aqueous solution (2.5 mL) and tert-butanol (2.5 mL). 3,3-Diethoxy-propyne (28.8 μL, 0.2 mmol) and sodium ascorbate (14.9 mg, 0.075 mmol) were added, and the mixture was reacted under a nitrogen atmosphere at 70° C. for 6 hr. After the reaction, the mixture was diluted with 20 wt % brine (10 mL), chloroform (20 mL) was added and the mixture was stirred under a nitrogen atmosphere at room temperature for 10 min. After stirring, the mixture was left standing for 10 min, and the organic layer was recovered. To the recovered organic layer was added magnesium sulfate, and the mixture was stirred at room temperature for 10 min. After stirring, the mixture was suction filtered. The filtrate obtained by filtration was diluted with toluene (100 g) and stirred at room temperature for 5 min. Thereafter, hexane (50 g) was added to precipitate crystals. The crystals were collected by suction filtration. The recovered crystals were dried, dissolved in phosphoric acid aqueous solution (50 g) at pH 1.7, and stirred under a nitrogen atmosphere at room temperature for 2 hr. After stirring, sodium hydroxide aqueous solution was added to adjust the mixture to pH 6.7 and sodium chloride (11.4 g) was dissolved. Thereafter, chloroform (24.0 g) was added, and the mixture was stirred under a nitrogen atmosphere at room temperature for 10 min. After stirring, the mixture was allowed to stand for 10 min and the organic layer was recovered. To the recovered organic layer was added magnesium sulfate to perform a dehydrating operation and the mixture was suction filtered. The obtained filtrate was diluted with toluene (150 g) and stirred for 5 min. Thereafter, hexane (75 g) was added to precipitate crystals. The crystals were collected by suction filtration. 2-Propanol (150 g) was added and the mixture was stirred under a nitrogen atmosphere at room temperature for 15 min. After stirring, the crystals were collected by suction filtration and dried to obtain compound (8) (mPEG(20k)-PhTA4C (4CB)) (2.2 g).

$^1$H-NMR ($d_6$-DMSO); 1.78 ppm (m, 2H, —$(CH_2CH_2O)_n$—$CH_2$—$CH_2$—$CH_2$—), 3.24 ppm (s, 3H, $CH_3$—O—$(CH_2CH_2O)_n$—), 3.64 ppm (m, about 1,800H, $CH_3$—O—$(CH_2CH_2O)_n$—), 8.06 ppm (m, 4H, —NH—CO—$(C_6H_4)$—), 8.63 ppm (m, 1H, —NH—CO—$(C_6H_4)$—), 9.66 ppm (s, 1H, —$(C_6H_4)$—$(C_2HN_3)$—CHO), 10.13 ppm (s, 1H, —$(C_6H_4)$—$(C_2HN_3)$—CHO)

[Example 4] Synthesis of Compound (10) (mPEG (40k)-PhTA4C (4CB)) Represented by the Following Formula (in the Following Formula, n is about 909)

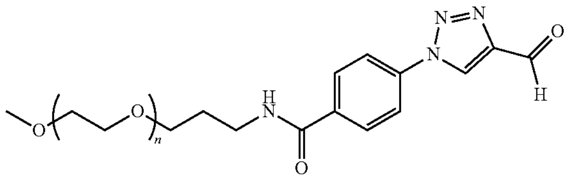

[Example 4-1] Synthesis of Compound (11) (mPEG (40k)-Ph-Azide (4CB)) Represented by the Following Formula (in the Following Formula, n is about 909)

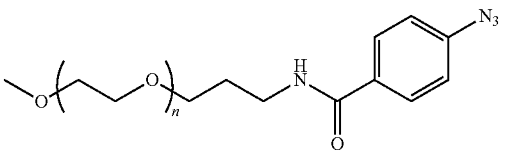

SUNBRIGHT MEPA-40T manufactured by NOF CORPORATION (number average molecular weight: 43,470) (5.0 g, 0.125 mmol) was dissolved in acetonitrile (20 g). 4-Azidobenzoic acid (30.6 mg, 0.188 mmol), DIPEA (32.0 μL, 0.188 mmol), and DMT-MM (130 mg, 0.375 mmol) were added, and the mixture was reacted under a nitrogen atmosphere at room temperature for 3 hr. The operation thereafter was performed in the same manner as in Example 3-1 to obtain compound (11) (mPEG(40k)-Ph-Azide (4CB)) (4.6 g).

[Example 4-2] Synthesis of Compound (10) (mPEG (40k)-PhTA4C (4CB))

Compound (11) (3.0 g, 0.075 mmol) obtained in Example 4-1 and BHT (3.0 mg) were dissolved in a mixed solution of 100 mM copper (II) sulfate aqueous solution (2.5 mL) and tert-butanol (2.5 mL). 3,3-Diethoxypropyne (14.4 μL, 0.1 mmol) and sodium ascorbate (7.4 mg, 0.038 mmol) were added, and the mixture was reacted under a nitrogen atmosphere at 70° C. for 6 hr. The operation thereafter was performed in the same manner as in Example 3-2 to obtain compound (10) (mPEG (40k)-PhTA4C (4CB)) (1.8 g).

$^1$H-NMR (de-DMSO); 1.78 ppm (m, 2H, —$(CH_2CH_2O)_n$—$CH_2$—$CH_2$—$CH_2$—), 3.24 ppm (s, 3H, $CH_3$—O—$(CH_2CH_2O)_n$—), 3.64 ppm (m, about 3, 600H, $CH_3$—O—$(CH_2CH_2O)_n$—), 8.06 ppm (m, 4H, —NH—CO—$(C_6H_4)$—), 8.63 ppm (m, 1H, —NH—CO—$(C_6H_4)$—), 9.66 ppm (s, 1H, —$(C_2HN_3)$—$(C_2HN_3)$—CHO), 10.13 ppm (s, 1H, —$(C_6H_4)$—$(C_2HN_3)$—CHO)

[Example 5] Synthesis of Compound (12) (mPEG (20k)-PhTA4C (4CB2MO)) Represented by the Following Formula (in the Following Formula, n is about 455)

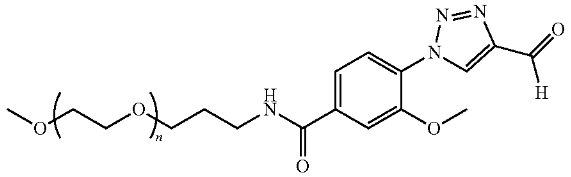

4-(4-Formyl-1H-1, 2, 3-triazol-1-yl)-5-methoxybenzoic acid (17.3 mg, 0.07 mmol) synthesized with reference to Tetrahedron Lett., 2017, 58, 4450-4454 and Medchem Lett., 2017, 27, 1119-1123 and DMT-MM (48.4 mg, 0.14 mmol) were dissolved in acetonitrile (4.8 g), and the mixture was stirred for 1 hr. Thereafter, SUNBRIGHT MEPA-20T manufactured by NOF CORPORATION (800 mg, 0.08 mmol) was added, and the mixture was reacted under a nitrogen atmosphere at room temperature for 3 hr. The operation thereafter was performed in the same manner as in Example 2 to obtain compound (12) (mPEG (40k)-PhTA4C (4CB2MO)) (736 mg).

$^1$H-NMR ($d_6$-DMSO); 1.78 ppm (m, 2H, —$(CH_2CH_2O)_n$—$CH_2$—$CH_2$—$CH_2$—), 3.24 ppm (s, 3H, $CH_3$—O—$(CH_2CH_2O)_n$—), 3.64 ppm (m, about 1, 800H, $CH_3$—O—$(CH_2CH_2O)_n$—), 3.95 ppm (s, 3H, —$(C_6H_3$ $(OCH_3))$—), 7.6-7.8 ppm (3H, —NH—CO—$(C_6H_3$ $(OCH_3))$—), 8.63 ppm (m, 1H, —NH—CO—$(C_6H_3$ $(OCH_3))$—), 9.27 ppm (s, 1H, —$(C_6H_3(OCH_3))$—$(C_2HN_3)$—CHO), 10.13 ppm (s, 1H, —$(C_6H_3$ $(OCH_3))$—$(C_2HN_3)$—CHO)

[Example 6] Synthesis of Compound (13) (mPEG (20k)-PhTA4C (3CB)) Represented by the Following Formula (in the Following Formula, n is about 455)

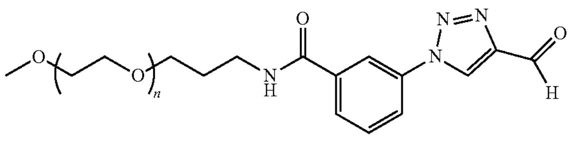

3-(4-Formyl-1H-1,2,3-triazol-1-yl)benzoic acid (3.8 mg, 0.018 mmol) synthesized with reference to Tetrahedron Lett., 2017, 58, 4450-4454 and Medchem Lett., 2017, 27, 1119-1123 and DMT-MM (12.1 mg, 0.035 mmol) were dissolved in acetonitrile (1.2 g), and the mixture was stirred for 1 hr. Thereafter, SUNBRIGHT MEPA-20T (200 mg, 0.01 mmol) manufactured by NOF CORPORATION was added, and the mixture was reacted under a nitrogen atmosphere at room temperature for 3 hr. The operation thereafter was performed in the same manner as in Example 2 to obtain compound (13) (mPEG(40k)-PhTA4C(3CB)) (153 mg).

$^1$H-NMR ($d_6$-DMSO); 1.78 ppm (m, 2H, —$(CH_2CH_2O)_n$—$CH_2$—$CH_2$—$CH_2$—), 3.24 ppm (s, 3H, $CH_3$—O—$(CH_2CH_2O)_n$—), 3.64 ppm (m, about 1, 800H, $CH_3$—O—$(CH_2CH_2O)_n$—), 7.7-8.4 ppm (4H, —NH—CO—$(C_6H_4)$—), 8.67 ppm (m, 1H, —NH—CO—$(C_6H_4)$—), 9.62 ppm (s, 1H, —$(C_6H_4)$—$(C_2HN_3)$—CHO), 10.14 ppm (s, 1H, —$(C_6H_4)$—$(C_2HN_3)$—CHO)

[Example 7] Synthesis of Compound (14) (mPEG (20k)-PhTA4C (3CB6MO)) Represented by the Following Formula (in the Following Formula, n is about 455)

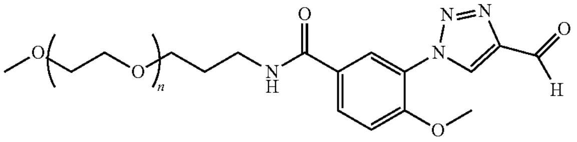

In the same manner as in Example 6 except that 3-(4-formyl-1H-1, 2, 3-triazol-1-yl)-4-methoxybenzonic acid (4.3 mg, 0.018 mmol) was used instead of 3-(4-formyl-1H-1, 2, 3-triazol-1-yl)benzoic acid, compound (14) (mPEG (20k)-PhTA4C(3CB6MO)) (178 mg) was obtained.

$^1$H-NMR ($d_6$-DMSO); 1.78 ppm (m, 2H, —$(CH_2CH_2O)_n$—$CH_2$—$CH_2$—$CH_2$—), 3.24 ppm (s, 3H, $CH_3$—O—$(CH_2CH_2O)_n$—), 3.64 ppm (m, about 1,800H, $CH_3$—O—$(CH_2CH_2O)_n$—), 3.92 ppm (s, 1H, —$(C_6H_3$ $(OCH_3))$—), 7.4-8.2 ppm (3H, —NH—CO—$(C_6H_3(OCH_3))$—), 8.54 ppm (m, 1H, —NH—CO—$(C_6H_3$ $(OCH_3))$—), 9.25 ppm (s, 1H, —$(C_6H_3$ $(OCH_3))$—$(C_2HN_3)$—CHO), 10.12 ppm (s, 1H, —$(C_6H_3$ $(OCH_3))$—$(C_2HN_3)$—CHO)

[Example 8] Synthesis of Compound (15) (mPEG (20k)-PhTA4C (3CB4MO)) Represented by the Following Formula (in the Following Formula, n is about 455)

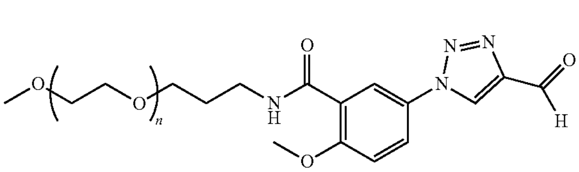

In the same manner as in Example 6 except that 3-(4-formyl-1H-1, 2, 3-triazol-1-yl)-6-methoxybenzoic acid (4.3 mg, 0.018 mmol) was used instead of 3-(4-formyl-1H-1, 2, 3-triazol-1-yl)benzoic acid, compound (15) (mPEG(20k)-PhTA4C(3CB4MO)) (178 mg) was obtained.

$^1$H-NMR ($d_6$-DMSO); 1.78 ppm (m, 2H, —$(CH_2CH_2O)_n$—$CH_2$—$CH_2$—$CH_2$—), 3.24 ppm (s, 3H, $CH_3$—O—$(CH_2CH_2O)_n$—), 3.64 ppm (m, about 1,800H, $CH_3$—O—$(CH_2CH_2O)_n$—), 3.97 ppm (s, 1H, —$(C_6H_3(OCH_3))$—) 7.4-8.3 ppm (3H, —NH—CO—$(C_6H_3(OCH_3))$—), 8.34 ppm (m, 1H, —NH—CO—$(C_6H_3$ $(OCH_3))$—), 9.55 ppm (s, 1H, —$(C_6H_3$ $(OCH_3))$—$(C_2HN_3)$—CHO), 10.11 ppm (s, 1H, —$(C_6H_3$ $(OCH_3))$—$(C_2HN_3)$—CHO)

[Example 9] Synthesis of Compound (16) (mPEG (20k)-PhTA4C ($3CB4NO_2$)) Represented by the Following Formula (in the Following Formula, n is about 455)

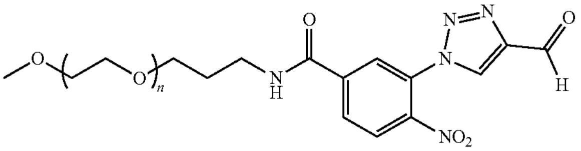

In the same manner as in Example 6 except that 3-(4-formyl-1H-1, 2, 3-triazol-1-yl)-4-nitrobenzoic acid (4.6 mg, 0.018 mmol) was used instead of 3-(4-formyl-1H-1, 2, 3-triazol-1-yl)benzoic acid, compound (16) (mPEG(20k)-PhTA4C ($3CB4NO_2$)) (171 mg) was obtained.

$^1$H-NMR (de-DMSO); 1.78 ppm (m, 2H, —$(CH_2CH_2O)_n$—$CH_2$—$CH_2$—$CH_2$—), 3.24 ppm (s, 3H, $CH_3$—O—$(CH_2CH_2O)_n$—), 3.64 ppm (m, about 1, 800H, $CH_3$—O—$(CH_2CH_2O)_n$—), 8.3 ppm (3H, —NH—CO—$(C_6H_3$ $(NO_2))$—), 8.81 ppm (m, 1H, —NH—CO—$(C_6H_3$ $(NO_2))$—), 9.78 ppm (s, 1H, —$(C_6H_3$ $(NO_2))$—$(C_2HN_3)$—CHO), 10.15 ppm (s, 1H, —$(C_6H_3$ $(NO_2))$—$(C_2HN_3)$—CHO)

[Example 10] Synthesis of Compound (17) ((mPEG $(10k))_2$-PhTA4C (3CB)) Represented by the Following Formula (in the Following Formula, n is about 227)

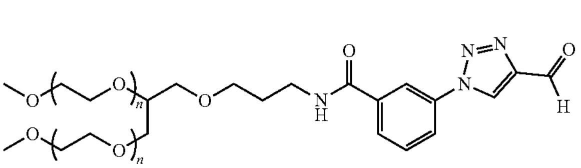

In the same manner as in Example 6 except that SUNBRIGHT GL2-200PA manufactured by NOF CORPORATION (number average molecular weight: 19,910) (200 mg, 0.01 mmol) was used instead of SUNBRIGHT MEPA-20T manufactured by NOF CORPORATION, compound (17) ((mPEG(10k)) 2-PhTA4C (3CB)) (148 mg) was obtained.

$^1$H-NMR ($d_6$-DMSO); 1.78 ppm (m, 2H, —$CH_2$—$CH_2$—$CH_2$—NH—CO—), 3.24 ppm (s, 6H, $(CH_3$—O—$(CH_2CH_2O)_n)_2$—), 3.64 ppm (m, about 1, 800H, $(CH_3$—O—$(CH_2CH_2O)_m)_2$—), 7.7-8.4 ppm (4H, —NH—CO—$(C_6H_4)$—), 8.67 ppm (m, 1H, —NH—CO—$(C_6H_4)$—), 9.62 ppm (s, 1H, —$(C_6H_4)$—$(C_2HN_3)$—CHO), 10.14 ppm (s, 1H, —$(C_6H_4)$—$(C_2HN_3)$—CHO)

[Example 11] Synthesis of Compound (18) (mPEG (20k)-PhTA4C5CH3) Represented by the Following Formula (in the Following Formula, n is about 455)

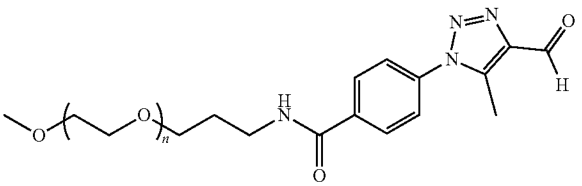

[Example 11-1] Synthesis of Compound (19) (mPEG (20k)-PhTA4C5CH3) Represented by the Following Formula (in the Following Formula, n is about 455)

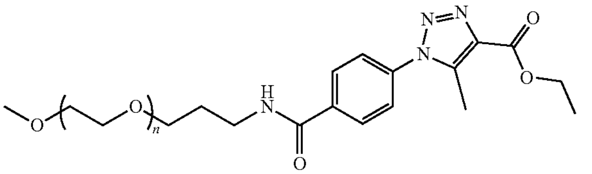

Compound (9) (2.0 g, 0.1 mmol) obtained in the same manner as in Example 3-1 and BHT (3.0 mg) were dissolved in a mixed solution of dimethyl sulfoxide (DMSO) (2.2 mL) and ion exchanged water (220 μL). Ethyl acetoacetate (253 μL, 2.0 mmol) and piperidine (39.6 μL, 0.4 mmol) were added, and the mixture was reacted under a nitrogen atmosphere at 80° C. for 6 hr. After the reaction, the mixture was diluted with dichloromethane (20 mL). To the diluted solution was added 20 wt % brine (20 mL) and the mixture was stirred under a nitrogen atmosphere at room temperature for 10 min. After stirring, the mixture was allowed to stand for 10 min and the organic layer was recovered. To the recovered organic layer was added magnesium sulfate, and the mixture was stirred at room temperature for 10 min and suction filtered. The filtrate obtained by filtration was concentrated and diluted with toluene (100 g), and stirred at room temperature for 5 min. Thereafter, hexane (50 g) was added to precipitate crystals. The crystals were collected by suction filtration and dried to obtain compound (19) (mPEG (20k)-PhTA4C5$CH_3$) (1.7 g).

[Example 11-2] Synthesis of Compound (20) (mPEG (20k)-PhTA4OH5CH3) Represented by the Following Formula (in the Following Formula, n is about 455)

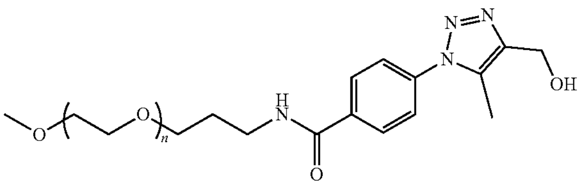

Compound (19) (500 mg, 0.013 mmol) obtained in Example 11-1 and sodium methoxide (2.4 mg, 0.013 mmol) were dissolved in methanol (1.25 mL), sodium borohydride (284 mg, 7.5 mmol) was added and the mixture was reacted under a nitrogen atmosphere at room temperature for 30 hr. After the reaction, 20 wt % brine (5 mL) was added and the mixture was stirred at room temperature for 5 min. Thereafter, dichloromethane (10 mL) was added and the mixture was stirred under a nitrogen atmosphere at room temperature for 10 min. After stirring, the mixture was allowed to stand for 10 min and the organic layer was recovered. The recovered organic layer was concentrated to dryness, redissolved in toluene (100 mL), and hexane (50 mL) was added to precipitate crystals. The crystals were collected by suction filtration and dried to obtain compound (20) (mPEG (20k)-PhTA4OH5CH3) (277 mg).

[Example 11-3] Synthesis of Compound (18) (mPEG (20k)-PhTA4C5CH3)

Compound (20) (200 mg, 0.01 mmol) obtained in Example 11-2 was dissolved in chloroform (1.0 mL). Dess-Martin reagent (25.4 mg, 0.06 mmol), chloroform (1.0 mL), and ion exchanged water (0.2 μL) were added, and the mixture was reacted under a nitrogen atmosphere at room temperature for 6 hr. After the reaction, the mixture was diluted with chloroform (5 mL), a mixed solvent of 10 wt % sodium thiosulfate (3.5 mL) and 5 wt % sodium hydrogen carbonate aqueous solution (3.5 mL) was added, and the mixture was stirred under a nitrogen atmosphere at room temperature for 10 min. After stirring, the mixture was allowed to stand for 10 min and the organic layer was recovered. To the recovered organic layer was added magnesium sulfate, and the mixture was stirred at room temperature for 10 min and suction filtered. The filtrate obtained by filtration was concentrated and diluted with toluene (100 g), and stirred at room temperature for 5 min. Thereafter, hexane (50 g) was-added to precipitate crystals. The crystals were collected by suction filtration and dried to obtain compound (18) (mPEG (20k)-PhTA4C5CH3) (55 mg).

$^1$H-NMR ($d_6$-DMSO); 1.78 ppm (m, 2H, —$(CH_2CH_2O)_n$—$CH_2$—$\underline{CH_2}$—$CH_2$—), 2.61 ppm (s, 3H, —$(C_6H_4)$—$(\underline{C_2(CH_3)\ N_3})$—CHO), 3.24 ppm (s, 3H, $\underline{CH_3}$—O—$(CH_2CH_2O)_n$—), 3.64 ppm (m, about 1,800H, $CH_3$—O—$(\underline{CH_2CH_2}O)_n$—), 7.7-8.1 ppm (m, 4H, —NH—CO—$(\underline{C_6H_4})$—), 8.66 ppm (m, 1H, —$\underline{NH}$—CO—$(C_6H_4)$—), 10.17 ppm (s, 1H, —$(C_6H_4)$—$(C_2\ (CH_3)\ N_3)$—$\underline{CHO}$)

[Example 12] Synthesis of Compound (21) (mPEG (20k)-PhTA4C5CHF2) Represented by the Following Formula (in the Following Formula, n is about 455)

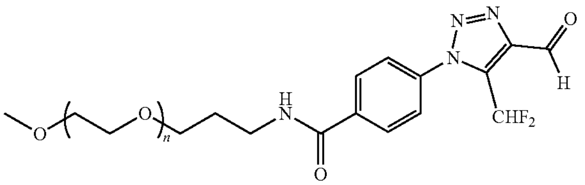

[Example 12-1] Synthesis of Compound (22) (mPEG (20k)-PhTA4Et5CHF2) Represented by the Following Formula (in the Following Formula, n is about 455)

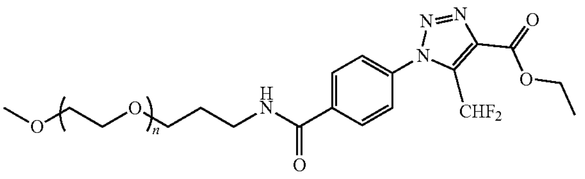

Compound (9) (1.0 g, 0.05 mmol) obtained in the same manner as in Example 3-1 and BHT (1.0 mg) were dissolved in a mixed solvent of DMSO (1.1 mL) and ion exchanged water (110 μL). Ethyl 4,4-difluoroacetoacetate (135 μL, 1.0 mmol) and piperidine (19.8 μL, 0.2 mmol) were added, and the mixture was reacted under a nitrogen atmosphere at 80° C. for 6 hr. After the reaction, an operation similar to that in Example 11-1 was performed to obtain compound (22) (mPEG (20k)-PhTA4Et5CHF2) (930 mg).

[Example 12-2] Synthesis of Compound (23) (mPEG (20k)-PhTA4OH5CHF2) Represented by the Following Formula (in the Following Formula, n is about 455)

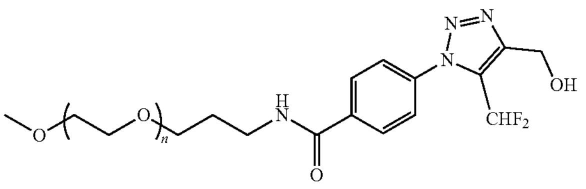

Compound (22) (700 mg, 0.035 mmol) obtained in Example 12-1 and sodium methoxide (20.3 mg, 0.105 mmol) were dissolved in methanol (3.15 mL), sodium borohydride (397 mg, 10.5 mmol) was added, and the mixture was reacted under a nitrogen atmosphere at room temperature for 8 hr. After the reaction, an operation similar to that in Example 11-2 was performed to obtain compound (23) (mPEG (20k)-PhTA4OH5CHF2) (590 mg).

[Example 12-3] Synthesis of Compound (21) (mPEG (20k)-PhTA4C5CHF2)

Compound (23) (300 mg, 0.015 mmol) obtained in Example 12-2 was dissolved in chloroform (1.5 mL). Dess-Martin reagent (38.2 mg, 0.09 mmol), chloroform (1.5 mL), and ion exchanged water (0.3 μL) were added and the mixture was reacted under a nitrogen atmosphere at room temperature for 6 hr. After the reaction, an operation similar to that in Example 11-3 was performed to obtain compound (21) (mPEG (20k)-PhTA4C5CHF2) (185 mg).

$^1$H-NMR ($d_6$-DMSO); 1.78 ppm (m, 2H, —$(CH_2CH_2O)_n$—$CH_2$—$\underline{CH_2}$—$CH_2$—), 3.24 ppm (s, 3H, $\underline{CH_3}$—O—$(CH_2CH_2O)_n$—), 3.64 ppm (m, about 1,800H, $CH_3$—O—$\underline{(CH_2CH_2O)_n}$—), 7.4-7.6 ppm (t, 1H, —$(C_6H_4)$—$(C_2$ $\underline{(CHF_2)}$ $N_3)$—CHO)) 7.7-8.1 ppm (4H, —NH—CO—$\underline{(C_6H_4)}$—), 8.68 ppm (m, 1H, —$\underline{NH}$—CO—$(C_6H_4)$—), 10.23 ppm (s, 1H, —$(C_6H_4)$—$(C_2$ $(CHF_2)$ $N_3)$—$\underline{CHO}$)

[Example 13] Synthesis of Compound (24) (mPEG (20k)-PhTA4C5Ph) Represented by the Following Formula (in the Following Formula, n is about 455)

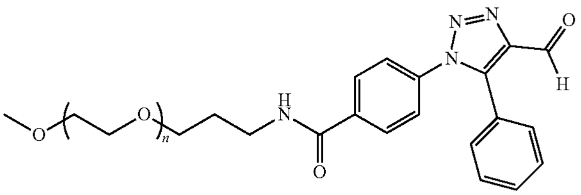

[Example 13-1] Synthesis of Compound (25) (mPEG (20k)-PhTA4Et5Ph) Represented by the Following Formula (in the Following Formula, n is about 455)

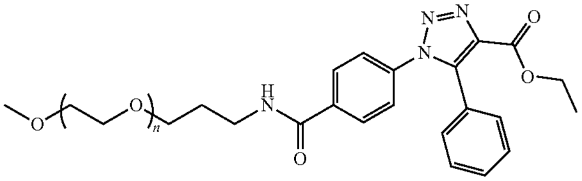

In the same manner as in Example 12-1 except that ethyl benzoylacetate (173 μL, 1.0 mmol) was used instead of ethyl 4,4-difluoroacetoacetate, compound (25) (mPEG (20k)-PhTA4Et5Ph) (925 mg) was obtained.

[Example 13-2] Synthesis of Compound (26) (mPEG (20k)-PhTA4OH5Ph) Represented by the Following Formula (in the Following Formula, n is about 455)

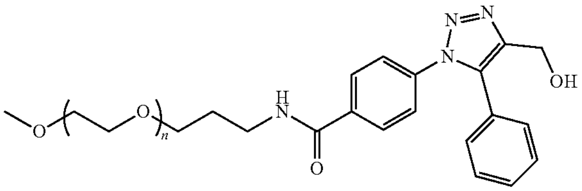

In the same manner as in Example 12-2 except that compound (25) (700 mg, 0.035 mmol) obtained in Example 13-1 was used instead of compound (22), compound (26) (mPEG (20k)-PhTA4OH5Ph) (349 mg) was obtained.

[Example 13-3] Synthesis of Compound (24) (mPEG (20k)-PhTA4C5Ph)

In the same manner as in Example 12-3 except that compound (26) (300 mg, 0.015 mmol) obtained in Example 13-2 was used instead of compound (23), compound (24) (136 mg) was obtained.

$^1$H-NMR ($d_6$-DMSO); 1.78 ppm (m, 2H, —$(CH_2CH_2O)_n$—$CH_2$—$\underline{CH_2}$—$CH_2$—), 3.24 ppm (s, 3H, $\underline{CH_3}$—O—$(CH_2CH_2O)_n$—), 3.64 ppm (m, about 1, 800H, $CH_3$—O—

$(CH_2CH_2O)_n$—), 7.4-8.1 ppm (9H, —$(C_6H_4)$—$(C_2\ (C_6H_5)\ N_3)$—CHO)), 8.68 ppm (m, 1H, —NH—CO—$(C_6H_4)$—), 10.23 ppm (s, 1H, —$(C_6H_4)$—$(C_2\ (C_6H_5)\ N_3)$—CHO)

[Example 14] Synthesis of Compound (27) (mPEG (20k)-PhTA4C5p-OCH3Ph) Represented by the Following Formula (in the Following Formula, n is about 455)

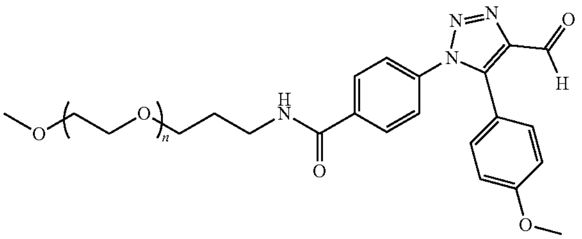

[Example 14-1] Synthesis of Compound (28) (mPEG (20k)-PhTA4Et5p-OCH3Ph) Represented by the Following Formula (in the Following Formula, n is about 455)

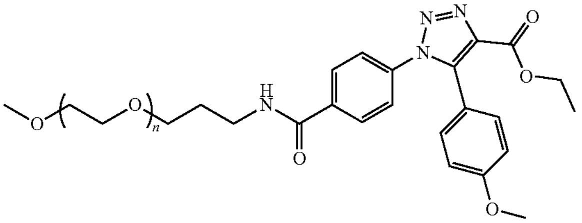

In the same manner as in Example 12-1 except that ethyl 4-methoxybenzoylacetate (192 μL, 1.0 mmol) was used instead of ethyl 4,4-difluoroacetoacetate, compound (28) (mPEG (20k)-PhTA4Et5p-$OCH_3Ph$) (796 mg) was obtained.

[Example 14-2] Synthesis of Compound (29) (mPEG (20k)-PhTA4OH5p-OCH3Ph) Represented by the Following Formula (in the Following Formula, n is about 455)

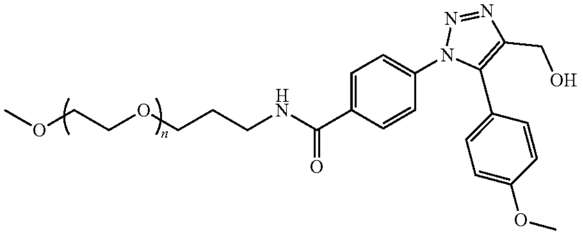

In the same manner as in Example 12-2 except that compound (28) (700 mg, 0.035 mmol) obtained in Example 14-1 was used instead of compound (22), compound (29) (mPEG (20k)-PhTA4OH5p-$OCH_3Ph$) (333 mg) was obtained.

[Example 14-3] Synthesis of Compound (27) (mPEG (20k)-PhTA4C5p-OCH3Ph)

In the same manner as in Example 12-3 except that compound (29) (300 mg, 0.015 mmol) obtained in Example 14-2 was used instead of compound (23), compound (27) (191 mg) was obtained.

$^1$H-NMR ($d_6$-DMSO); 1.76 ppm (m, 2H, —$(CH_2CH_2O)_n$—$CH_2$—$CH_2$—$CH_2$—), 3.24 ppm (s, 3H, $CH_3$—O—$(CH_2CH_2O)_n$—), 3.64 ppm (m, about 1, 800H, $CH_3$—O—$(CH_2CH_2O)_n$—), 3.83 ppm (s, 3H, —$(CH_4)$—$(C_2\ (C_6H_4\ (CH_3))\ N_3)$-), 6.9-7.9 ppm (8H, —$(C_6H_4)$—$(C_2\ (C_6H_4\ (CH_3))\ N_3)$—), 8.58 ppm (m, 1H, —NH—CO—$(C_6H_4)$—), 10.03 ppm (s, 1H, —$(C_2\ (C_6H_4\ (CH_3))\ N_3)$—CHO)

[Example 15] Synthesis of Compound (30) (mPEG (20k)-PhTA4C5p-NO2Ph) Represented by the Following Formula (in the Following Formula, n is about 455)

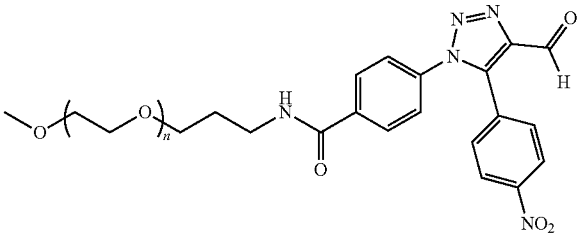

[Example 15-1] Synthesis of Compound (31) (mPEG (20k)-PhTA4Et5p-NO2Ph) Represented by the Following Formula (in the Following Formula, n is about 455)

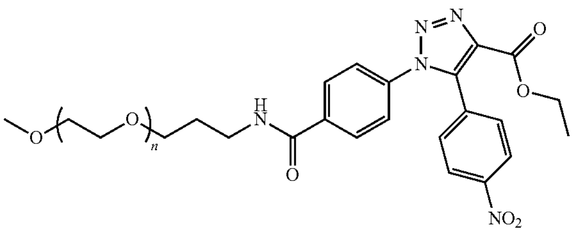

In the same manner as in Example 12-1 except that ethyl 4-nitrobenzoylacetate (192 μL, 1.0 mmol) was used instead of ethyl 4,4-difluoroacetoacetate, compound (31) (mPEG (20k)-PhTA4Et5p-NO2Ph) (813 mg) was obtained.

[Example 15-2] Synthesis of Compound (32) (mPEG (20k)-PhTA4OH5p-NO2Ph) Represented by the Following Formula (in the Following Formula, n is about 455)

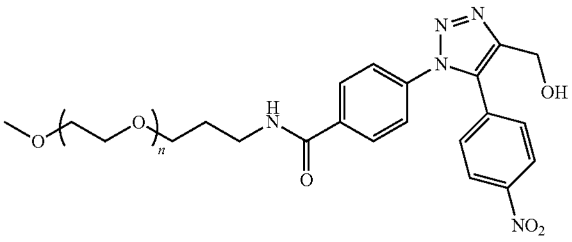

In the same manner as in Example 12-2 except that compound (31) (700 mg, 0.035 mmol) obtained in Example 15-1 was used instead of compound (22), compound (32) (mPEG (20k)-PhTA4OH5p-NO2Ph) (511 mg) was obtained.

[Example 15-3] Synthesis of Compound (30) (mPEG (20k)-PhTA4C5p-NO2Ph)

In the same manner as in Example 12-3 except that compound (32) (300 mg, 0.015 mmol) obtained in Example 15-2 was used instead of compound (23), compound (30) (154 mg) was obtained.

$^1$H-NMR ($d_6$-DMSO); 1.76 ppm (m, 2H, —$(CH_2CH_2O)_n$—$CH_2$—$CH_2$—$CH_2$—), 3.24 ppm (s, 3H, $CH_3$—O—$(CH_2CH_2O)_n$—), 3.64 ppm (m, about 1, 800H, $CH_3$—O—$(CH_2CH_2O)_n$—), 7.5-8.3 ppm (8H, —$(C_6H_4)$—$(C_2$ $(C_6H_4$ $(NO_2))$ $N_3)$—), 8.58 ppm (m, 1H, —NH—CO—$(C_6H_4)$—), 10.13 ppm (s, 1H, —$(C_2$ $(C_6H_4$ $(NO_2))$ $N_3)$—CHO)

[Example 16] Synthesis of Compound (33) (mPEG (20k)-PhTA4C50-FPh) Represented by the Following Formula (in the Following Formula, n is about 455)

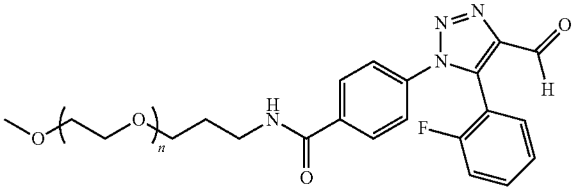

[Example 16-1] Synthesis of Compound (34) (mPEG (20k)-PhTA4Et5o-FPh) Represented by the Following Formula (in the Following Formula, n is about 455)

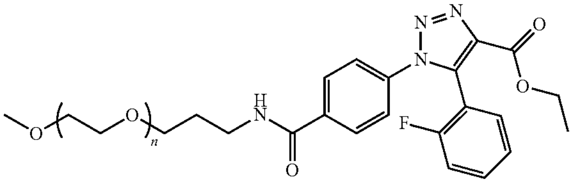

In the same manner as in Example 12-1 except that ethyl (4-fluorobenzoyl)acetate (178 μL, 1.0 mmol) was used instead of ethyl 4,4-difluoroacetoacetate, compound (34) (mPEG (20k)-PhTA4Et50-FPh) (923 mg) was obtained.

[Example 16-2] Synthesis of Compound (35) (mPEG (20k)-PhTA4OH5o-FPh) Represented by the Following Formula (in the Following Formula, n is about 455)

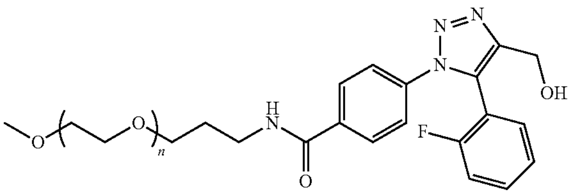

In the same manner as in Example 12-2 except that compound (34) (700 mg, 0.035 mmol) obtained in Example 16-1 was used instead of compound (22), compound (35) (mPEG (20k)-PhTA4OH50-FPh) (633 mg) was obtained.

[Example 16-3] Synthesis of Compound (33) (mPEG (20k)-PhTA4C50-FPh)

In the same manner as in Example 12-3 except that compound (35) (300 mg, 0.015 mmol) obtained in Example 16-2 was used instead of compound (23), compound (34) (214 mg) was obtained.

$^1$H-NMR ($d_6$-DMSO); 1.76 ppm (m, 2H, —$(CH_2CH_2O)_n$—$CH_2$—$CH_2$—$CH_2$—), 3.24 ppm (s, 3H, $CH_3$—O—$(CH_2CH_2O)_n$—), 3.64 ppm (m, about 1,800H, $CH_3$—O—$(CH_2CH_2O)_n$—), 7.3-7.9 ppm (8H, —$(C_6H_4)$—$(C_2$ $(C_6H_4F)$ $N_3)$—), 8.58 ppm (m, 1H, —NH—CO—$(C_6H_4)$—), 10.13 ppm (s, 1H, —$(C_2$ $(C_6H_4F)$ $N_3)$—CHO)

[Example 17] Synthesis of Compound (37) (mPEG (20k)-biPhTA4C5CF3) Represented by the Following Formula

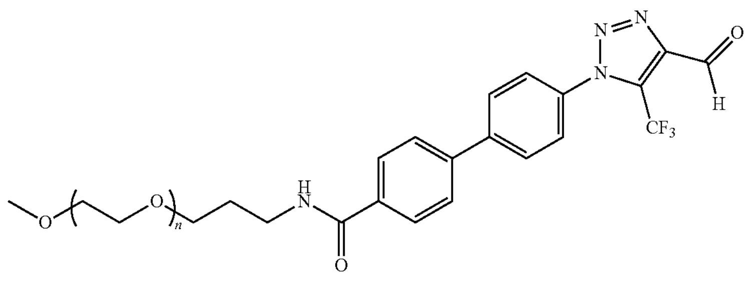

In the same manner as in Example 6 except that 4-(4-(4-formyl-5-trifluoromethyl-1, 2, 3-triazol-1-yl)phenyl)benzoic acid (6.3 g, 0.018 mmol) was used instead of 3-(4-formyl-1H-1, 2, 3-triazol-1-yl)benzoic acid, compound (37) (125 mg) was obtained.

$^1$H-NMR ($d_6$-DMSO); 1.78 ppm (m, 2H, —$(CH_2CH_2O)_n$—$CH_2$—$\underline{CH_2}$—$CH_2$—), 3.24 ppm (s, 3H, $\underline{CH_3}$—O—$(CH_2CH_2O)_n$—), 3.64 ppm (m, about 1, 800H, $CH_3$—O—$\underline{(CH_2CH_2O)_n}$—), 7.7-8.1 ppm (8H, —NH—CO—$\underline{(C_6H_4)}$—$\underline{(C_6H_4)}$—), 8.68 ppm (m, 1H, —$\underline{NH}$—CO—$(C_6H_4)$—), 10.23 ppm (s, 1H, —$(C_6H_4)$—$(C_6H_4)$—$(C_2\ (CF_3)\ N_3)$—$\underline{CHO}$)

[Example 18] Synthesis of Compound (38) (mPEG (20k)-BzTA4-LGG) Represented by the Following Formula (in the Following Formula, n is about 455)

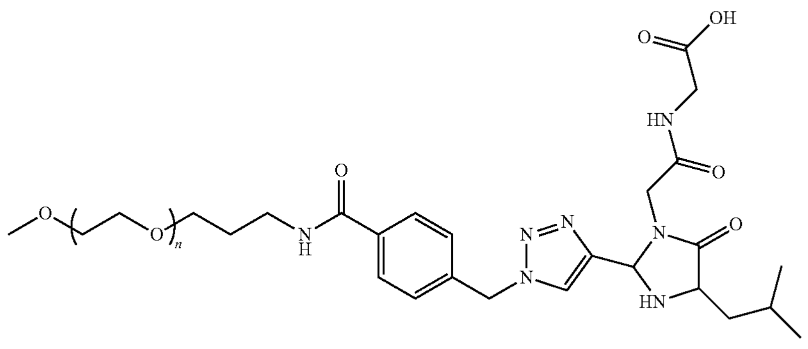

Compound (6) (450 mg (22.5 μmol) obtained in Example 1 and tripeptide (Leu-Gly-Gly) (55.2 mg, 225 μmol) were dissolved in 100 mM phosphate buffer (pH 7.4) (4.5 mL). Under a nitrogen atmosphere, the mixture was reacted at 40° C. for 24 hr. After the reaction, sodium chloride (1.3 g) was added, and the mixture was stirred at room temperature for 10 min. After stirring, chloroform (10 mL) was added and the mixture was stirred under a nitrogen atmosphere at room temperature for 10 min. After stirring, the mixture was left standing for 10 min and the organic layer was recovered. To the recovered organic layer was added magnesium sulfate, and the mixture was stirred at room temperature for 10 min and suction filtered. The filtrate obtained by filtration was concentrated, diluted with toluene (100 g), and stirred at room temperature for 5 min. Thereafter, hexane (50 g) was added to precipitate crystals. The crystals were collected by suction filtration and dried to obtain compound (38) (mPEG (20k)-BzTA4-LGG) (369 mg).

$^1$H-NMR ($D_2O$); 0.95 ppm (m, 6H, —$CH_2$—$C(\underline{CH_3})_2$), 1.6-1.7 ppm (m, 3H), 1.90 ppm (m, 2H, —$(CH_2CH_2O)_n$—$CH_2$—$\underline{CH_2}$—$CH_2$—), 3.39 ppm (s, 3H, $\underline{CH_3}$—O—$(CH_2CH_2O)_n$—), 3.64 ppm (m, about 1,800H, $CH_3$—O—$\underline{(CH_2CH_2O)_n}$—), 5.74 ppm (d, 2H, —$(C_6H_4)$—$\underline{CH_2}$—$(C_2HN_3)$—), 5.8 ppm (d, 1H), 7.4-7.8 ppm (4H, —$\underline{(C_6H_4)}$—$CH_2$—$(C_2HN_3)$—), 8.22 ppm (d, 1H, —$(C_6H_4)$—$CH_2$—$\underline{(C_2HN_3)}$—)

[Example 19] Synthesis of Compound (39) (mPEG (10k)-BzTA4-LGG) Represented by the Following Formula (in the Following Formula, n is about 227)

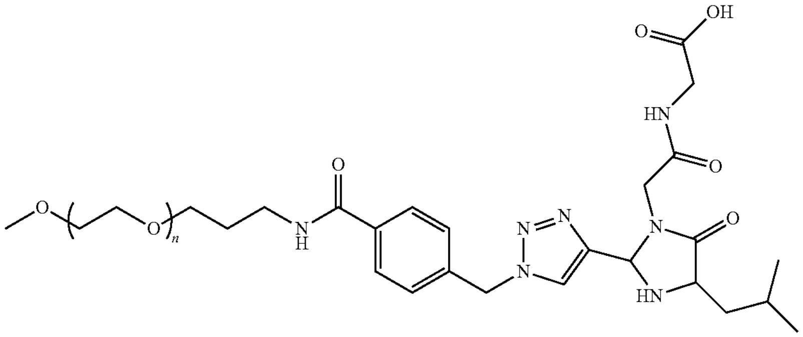

Compound (7) (600 mg (60 μmol) obtained in Example 2 and tripeptide (Leu-Gly-Gly) (147.2 mg, 600 μmol) were dissolved in 100 mM phosphate buffer (pH 7.4, 6.0 mL) and reacted under a nitrogen atmosphere at 40° C. for 24 hr. After the reaction, an operation similar to that in Example 18 was performed to obtain compound (39) (mPEG (10k)-BzTA4-LGG) (535 mg).

$^1$H-NMR ($D_2O$); 0.95 ppm (m, 6H, —$CH_2$—$C(\underline{CH_3})_2$), 1.6-1.7 ppm (m, 3H), 1.90 ppm (m, 2H, —$(CH_2CH_2O)_n$—$CH_2$—$\underline{CH_2}$—$CH_2$—), 3.39 ppm (s, 3H, $\underline{CH_3}$—O—$(CH_2CH_2O)_n$—), 3.64 ppm (m, about 1, 800H, $CH_3$—O—$(\underline{CH_2CH_2O})_n$—), 5.74 ppm (d, 2H, —$(C_6H_4)$—$\underline{CH_2}$—$(C_2HN_3)$—), 5.8 ppm (d, 1H), 7.4-7.8 ppm (4H, —$(\underline{C_6H_4})$—$CH_2$—$(C_2HN_3)$—), 8.22 ppm (d, 1H, —$(C_6H_4)$—$CH_2$—$(\underline{C_2HN_3})$—)

[Example 20] Synthesis of Compound (40) (mPEG (20k)-PhTA4 (4CB)-LGG) Represented by the Following Formula (in the Following Formula, n is about 455)

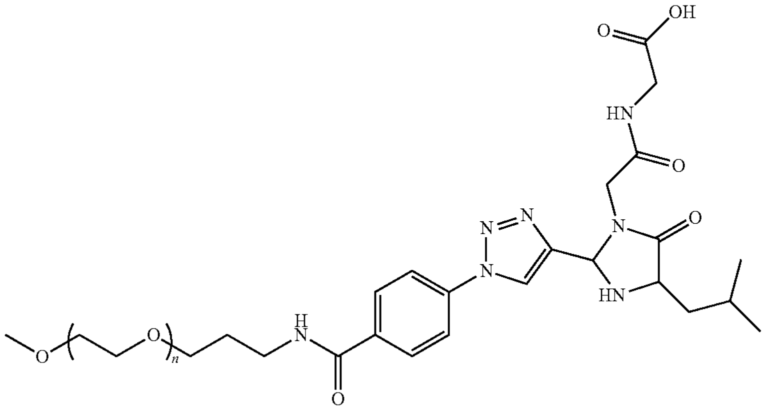

Compound (8) (1.0 g, 50 μmol) obtained in Example 3-3 and tripeptide (Leu-Gly-Gly) (122.6 mg, 500 μmol) were dissolved in 100 mM phosphate buffer (pH 7.4, 10 mL), and reacted under a nitrogen atmosphere at 40° C. for 24 hr. After the reaction, an operation similar to that in Example 18 was performed to obtain compound (40) (mPEG (20k)-PhTA4 (4CB)-LGG) (877 mg).

$^1$H-NMR ($D_2O$); 0.95 ppm (m, 6H, —$CH_2$—C($\underline{CH_3}$)$_2$), 1.6-1.7 ppm (m, 3H), 1.90 ppm (m, 2H, —$(CH_2CH_2O)_n$—$CH_2$—$\underline{CH_2}$—$CH_2$—), 3.39 ppm (s, 3H, $\underline{CH_3}$—O—$(CH_2CH_2O)_n$—), 3.64 ppm (m, about 1,800H, $CH_3$—O—$\underline{(CH_2CH_2O)_n}$—), 5.8 ppm (d, 1H), 7.4-7.8 ppm (4H, —$\underline{(C_6H_4)}$—$(C_2HN_3)$—), 8.22 ppm (d, 1H, —$(C_6H_4)$—$\underline{(C_2HN_3)}$—)

[Example 21] Synthesis of Compound (41) (mPEG (40k)-PhTA4 (4CB)-LGG) Represented by the Following Formula (in the Following Formula, n is about 909)

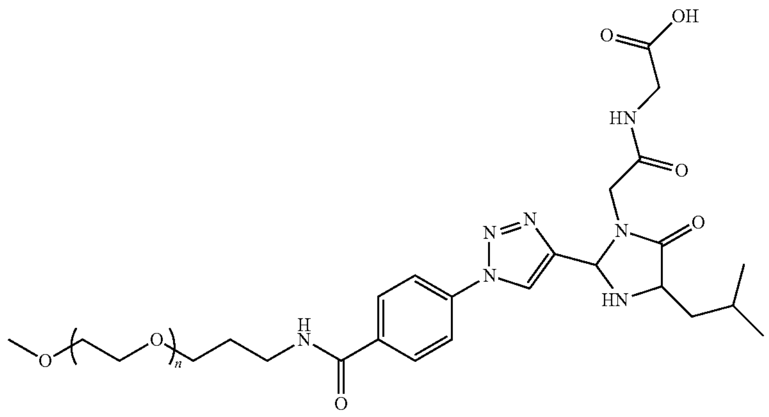

Compound (10) (800 mg, 20 ρmol) obtained in Example 4-2 and tripeptide (Leu-Gly-Gly) (49.1 mg, 200 μmol) were dissolved in 100 mM phosphate buffer (pH 7.4, 4 mL) and reacted under a nitrogen atmosphere at 40° C. for 24 hr. After the reaction, an operation similar to that in Example 18 was performed to obtain compound (41) (mPEG (40k)-PhTA4 (4CB)-LGG) (621 mg).

$^1$H-NMR ($D_2O$); 0.95 ppm (m, 6H, —$CH_2$—C($\underline{CH_3}$)$_2$), 1.6-1.7 ppm (m, 3H), 1.90 ppm (m, 2H, —$(CH_2CH_2O)_n$—$CH_2$—$\underline{CH_2}$—$CH_2$—), 3.39 ppm (s, 3H, $\underline{CH_3}$—O—$(CH_2CH_2O)_n$—), 3.64 ppm (m, about 1,800H, $CH_3$—O—$\underline{(CH_2CH_2O)_n}$—), 5.8 ppm (d, 1H), 7.4-7.8 ppm (4H, —$\underline{(C_6H_4)}$—$(C_2HN_3)$—), 8.22 ppm (d, 1H, —$(C_6H_4)$—$\underline{(C_2HN_3)}$—)

[Example 22] Synthesis of Compound (42) (mPEG (40k)-PhTA4 (4CB2MO)-LGG) Represented by the Following Formula (in the Following Formula, n is about 455)

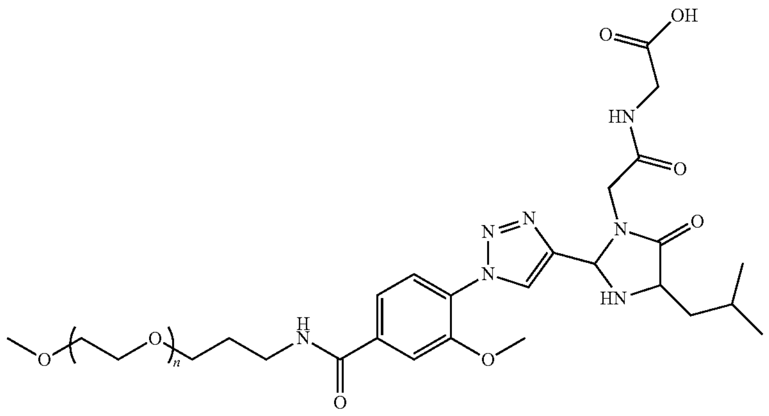

In the same manner as in Example 19 except that compound (12) (600 mg, 30 μmmol) obtained in Example 5 was used instead of compound (2), compound (42) (532 mg) was obtained.

$^1$H-NMR ($D_2O$); 0.95 ppm (m, 6H, —$CH_2$—$C(CH_3)_2$), 1.6-1.7 ppm (m, 3H), 1.90 ppm (m, 2H, —$(CH_2CH_2O)_n$—$CH_2$—$CH_2$—$CH_2$—), 3.39 ppm (s, 3H, $CH_3$—O—$(CH_2CH_2O)_n$—), 3.95 ppm (s, 3H, —($C_6H_3$ ($OCH_3$))—), 3.64 ppm (m, about 1,800H, $CH_3$—O—$(CH_2CH_2O)_n$—), 5.8 ppm (d, 1H), 7.4-7.8 ppm (3H, —($C_6H_3$ ($OCH_3$))—($C_2HN_3$)—), 8.22 ppm (d, 1H, —($C_6H_4$)—($C_2HN_3$)—)

[Experimental Example 1] Degradability Test

Compounds (38) to (42) obtained in Examples 18 to 22 were each dissolved in PBS (35 mL) at an amount of 350 mg, and the obtained solution was divided by 10 mL and each was subjected to Slide-A-Lyzer Dialysis Cassette G2, 10,000 MWCO (manufactured by ThermoFisher Scientific, dialysis cassette). The dialysis cassette containing the solution of each compound was immersed in 2 L of phosphate buffered saline (PBS) and maintained at 37° C. A portion of the solution of each compound in the dialysis cassette was sampled at a predetermined retention time and $^1$H-NMR was measured. FIG. 1 is a graph showing the amount of Leu-Gly-Gly adduct at each retention time, where the amount of Leu-Gly-Gly adduct in each compound at retention 0 hr is taken as 100%. Based on the formula obtained by exponentially approximating the graph, the degradation half-life ($t_{1/2}$) was calculated from the following calculation formula $$t_{1/2} = \text{In}(2)/\lambda$$

(In is the logarithm to the base of the Napier's constant, and λ is the product of the power exponent of the Napier's constant in the approximation formula and −1). It was 4.1 days for compound (38), 4.6 days for compound (39), 6.4 days for compound (40), 6.2 days for compound (41), and 5.1 days for compound (42). From these results, it was shown that the compounds (38) to (42) of the present invention have a significantly longer degradation half-life under physiological conditions compared to the degradation half-life of 12-18 hours for the compound described in Example 18 of WO 2020/175680.

[Example 23] Synthesis of Conjugate of Polyoxyethylene Derivative (Compound (10)) and RNase A Compound (10) (25 mg (1.25 μmol) obtained in Example 4-2 and RNase A (manufactured by Roche) (1.75 mg, 0.13 μmol) were dissolved in 100 mM borate buffer (pH 8.5, 250 μL) and reacted at 37° C. for 24 hr. After the reaction, unreacted compound (10) and RNase A were removed by cation exchange column chromatography using HiTrap SP-HP (manufactured by Cytiva). It was confirmed by HPLC analysis using reversed-phase column under the following conditions that a conjugate of compound (10) and RNase A bonded at 1:1 was obtained at a purity of 83.8%.

HPLC apparatus: Nexera
column: SunShell HFC18 (3.0×150 mm, 3 μm)
flow rate: 0.6 mL/min
column temperature: 40° C.
detector: PDA (measurement wavelength: 280 nm)
mobile phase A: 0.05% by volume trifluoroacetic acid (TFA)/water
mobile phase B: 0.05% by volume TFA/acetonitrile
gradient program (A/B): 80/20 (0 min)→40/60 (15 min) →0/100 (16 min)→0/100 (30 min)

INDUSTRIAL APPLICABILITY

Using the releasable polyoxyethylene derivative of the present invention, a conjugate with a polypeptide capable of functioning as a biofunctional molecule, wherein the conjugate can be degraded over a long time under physiological conditions to release the aforementioned polypeptide, can be formed. Such conjugate is expected to be usable as a prodrug.

This application is based on a patent application No. 2023-018695 filed in Japan, the contents of which are incorporated in full herein.

The invention claimed is:

1. A polyoxyethylene derivative represented by the formula (1):

(1)

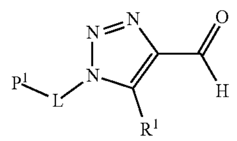

wherein $R^1$ is a hydrogen atom, an alkyl group having 1 to 4 carbon atoms, a halogenated alkyl group having 1 to 4 carbon atoms, an alkoxy group having 1 to 4 carbon atoms, a halogenated alkoxy group having 1 to 4 carbon atoms, an acyl group having 2 to 5 carbon atoms, an alkoxycarbonyl group having 2 to 5 carbon atoms, a carbamoyl group having 2 to 5 carbon atoms, an acyloxy group having 2 to 5 carbon atoms, a acylamino group having 2 to 5 carbon atoms, an alkoxycarbonylamino group having 2 to 5 carbon atoms, an alkylsulfanyl group having 1 to 4 carbon atoms, an alkylsulfonyl group having 1 to 4 carbon atoms, an arylsulfonyl group having 6 to 10 carbon atoms, a nitro group, a trifluoromethyl group, a cyano group, or an optionally-substituted phenyl group, $P^1$ is a group containing a polyoxyethylene chain having a number average molecular weight of 5,000 to 50,000, and L is a divalent spacer represented by the formula (2):

(2)

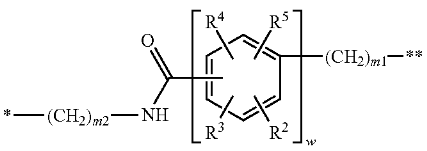

wherein m1 is 0 or 1, m2 is an integer of 1 to 3, w is 1 or 2, $R^2$, $R^3$, $R^4$, and $R^5$ are each independently a hydrogen atom, a halogen atom, an alkyl group having 1 to 4 carbon atoms, a halogenated alkyl group having 1 to 4 carbon atoms, an alkoxy group having 1 to 4 carbon atoms, a halogenated alkoxy group having 1 to 4 carbon atoms, an acyl group having 2 to 5 carbon atoms, an alkoxycarbonyl group having 2 to 5 carbon atoms, a carbamoyl group having 2 to 5 carbon atoms, an acyloxy group having 2 to 5 carbon atoms, an acylamino group having 2 to 5 carbon atoms, an alkoxycarbonylamino group having 2 to 5 carbon atoms, an alkylsulfanyl group having 1 to 4 carbon atoms, an alkylsulfonyl group having 1 to 4 carbon atoms, an arylsulfonyl group having 6 to 10 carbon atoms, a nitro group, a trifluoromethyl group, or a cyano group,

* is a bonding point with $P^1$, and

** is a bonding point with N.

2. The polyoxyethylene derivative according to claim 1, wherein m1 is 0 and w is 1.

3. A conjugate of the polyoxyethylene derivative according to claim 1 and a polypeptide, wherein the polypeptide is a biofunctional substance.

4. The conjugate according to claim 3 which is represented by the formula (3):

(3)

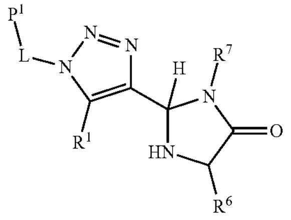

wherein $R^1$ is a hydrogen atom, an alkyl group having 1 to 4 carbon atoms, a halogenated alkyl group having 1 to 4 carbon atoms, an alkoxy group having 1 to 4 carbon atoms, a halogenated alkoxy group having 1 to 4 carbon atoms, an acyl group having 2 to 5 carbon atoms, an alkoxycarbonyl group having 2 to 5 carbon atoms, a carbamoyl group having 2 to 5 carbon atoms, an acyloxy group having 2 to 5 carbon atoms, a acylamino group having 2 to 5 carbon atoms, an alkoxycarbonylamino group having 2 to 5 carbon atoms, an alkylsulfanyl group having 1 to 4 carbon atoms, an alkylsulfonyl group having 1 to 4 carbon atoms, an arylsulfonyl group having 6 to 10 carbon atoms, a nitro group, a trifluoromethyl group, a cyano group, or an optionally-substituted phenyl group, $R^6$ is a side chain of an amino acid residue, $R^7$ is a group formed by removing —NH— from a terminal of an amino acid residue or a polypeptide chain, $P^1$ is a group containing a polyoxyethylene chain having a number average molecular weight of 5,000 to 50,000, and L is a divalent spacer represented by the formula (2):

(2)

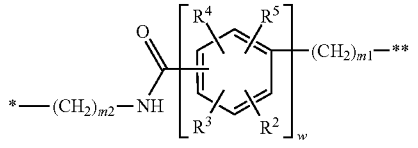

wherein m1 is 0 or 1, m2 is an integer of 1 to 3, w is 1 or 2, $R^2$, $R^3$, $R^4$, and $R^5$ are each independently a hydrogen atom, a halogen atom, an alkyl group having 1 to 4 carbon atoms, a halogenated alkyl group having 1 to 4 carbon atoms, an alkoxy group having 1 to 4 carbon atoms, a halogenated alkoxy group having 1 to 4 carbon atoms, an acyl group having 2 to 5 carbon atoms, an alkoxycarbonyl group having 2 to 5 carbon atoms, a carbamoyl group having 2 to 5 carbon atoms, an acyloxy group having 2 to 5 carbon atoms, an acylamino group having 2 to 5 carbon atoms, an alkoxycarbonylamino group having 2 to 5 carbon atoms, an alkylsulfanyl group having 1 to 4 carbon atoms, an alkylsulfonyl group having 1 to 4 carbon atoms, an arylsulfonyl group having 6 to 10 carbon atoms, a nitro group, a trifluoromethyl group, or a cyano group,

* is a bonding point with $P^1$, and

** is a bonding point with N.

5. The conjugate according to claim 4, wherein the polypeptide is a cytokine, a hormone, an antibody, an enzyme, a growth factor, or a blood coagulation factor.

6. The conjugate according to claim 4, wherein m1 is 0 and w is 1.

7. The conjugate according to claim 6, wherein the polypeptide is a cytokine, a hormone, an antibody, an enzyme, a growth factor, or a blood coagulation factor.

8. A conjugate of the polyoxyethylene derivative according to claim 2 and a polypeptide, wherein the polypeptide is a biofunctional substance.

9. The conjugate according to claim 8, wherein the polypeptide is a cytokine, a hormone, an antibody, an enzyme, a growth factor, or a blood coagulation factor.

10. The conjugate according to claim 3, wherein the polypeptide is a cytokine, a hormone, an antibody, an enzyme, a growth factor, or a blood coagulation factor.

* * * * *